(12) United States Patent
Sugiyama et al.

(10) Patent No.: US 10,945,942 B2
(45) Date of Patent: Mar. 16, 2021

(54) STARTING MATERIAL FOR COSMETICS

(71) Applicant: SHISEIDO COMPANY, LTD., Tokyo (JP)

(72) Inventors: Yuki Sugiyama, Yokohama (JP); Hirohito Shirakami, Yokohama (JP); Kazuyuki Miyazawa, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 240 days.

(21) Appl. No.: 15/501,989

(22) PCT Filed: Jun. 30, 2015

(86) PCT No.: PCT/JP2015/068861
§ 371 (c)(1),
(2) Date: Feb. 6, 2017

(87) PCT Pub. No.: WO2016/021338
PCT Pub. Date: Feb. 11, 2016

(65) Prior Publication Data
US 2017/0239165 A1    Aug. 24, 2017

(30) Foreign Application Priority Data
Aug. 6, 2014  (JP) .............................. JP2014-160441

(51) Int. Cl.
| | |
|---|---|
| *A61K 8/04* | (2006.01) |
| *A61K 8/81* | (2006.01) |
| *A61K 8/86* | (2006.01) |
| *A61Q 19/00* | (2006.01) |
| *A61K 8/34* | (2006.01) |
| *A61Q 5/06* | (2006.01) |
| *A61K 8/06* | (2006.01) |
| *A61K 8/31* | (2006.01) |
| *A61K 8/36* | (2006.01) |
| *A61K 8/58* | (2006.01) |
| *A61Q 1/00* | (2006.01) |
| *A61Q 17/04* | (2006.01) |
| *A61Q 19/02* | (2006.01) |
| *A61Q 19/10* | (2006.01) |

(52) U.S. Cl.
CPC ............ *A61K 8/8152* (2013.01); *A61K 8/042* (2013.01); *A61K 8/062* (2013.01); *A61K 8/31* (2013.01); *A61K 8/342* (2013.01); *A61K 8/345* (2013.01); *A61K 8/361* (2013.01); *A61K 8/585* (2013.01); *A61K 8/86* (2013.01); *A61Q 1/00* (2013.01); *A61Q 5/06* (2013.01); *A61Q 17/04* (2013.01); *A61Q 19/00* (2013.01); *A61Q 19/007* (2013.01); *A61Q 19/02* (2013.01); *A61Q 19/10* (2013.01); *A61K 2800/30* (2013.01); *A61K 2800/412* (2013.01); *A61K 2800/54* (2013.01)

(58) Field of Classification Search
None
See application file for complete search history.

(56) References Cited

FOREIGN PATENT DOCUMENTS

| | | |
|---|---|---|
| JP | 2004-203764 | 7/2004 |
| JP | 2005-132750 | 5/2005 |
| JP | 2006-160725 | 6/2006 |
| JP | 2006-161026 | 6/2006 |
| JP | 2006-161027 | 6/2006 |
| JP | 2011-132220 | 7/2011 |
| JP | 2013-147486 | 8/2013 |
| WO | WO-2013094298 A1 * | 6/2013 .......... C08F 290/062 |

OTHER PUBLICATIONS

English Translation of WO2013094298 retrieved from Espacenet on Mar. 2, 2018. (Year: 2013).*
PCT/JP2015/068861, ISR and Written Opinion, dated Aug. 25, 2015, 8 pages—Japanese, pages—English.
Emulsions stabilixed solely by colloidal particles, B. Binks et al., Advances in Colloid and Interface Science, 100-102 (2003), pp. 503-546, dated Jul. 18, 2002, The University of Hull, UK.
Factors Controlling the Stability of Colloid-Stabilized Emulsions, Mukul M. Sharma, et al., Journal of Colloid and Interface Science, 157, pp. 244-253, The University of Texas at Austin, accepted Nov. 4, 1992, Copyright 1993 by Academic Press, Inc.
JP 2014-160441, English translation of Japanese claims, 4 pages—English.
JP 2014-160441, English translation of Notice of Allowance dated Mar. 15, 2016, 3 pgs.—English, 3 pgs.—Japanese.
Particle Stabilizing Effects of Flavonoids at he Oil-Water Interface, Zijun Luo, et al., published Feb. 18, 2011, Journal of Agricultural and Food Chemistry, School of Food Science and Nutrition, University of Leeds, UK, ACS Publications, 2011, 10 pgs.
Swelling behavior of PMMA-g-PEO microgel particles by organic solvents, Isamu Kaneda, et al., Journal of Colloid and Interfae Science 274 (2004) pp. 49-54, Material Science Research Center, Shiseido co., Ltd., Japan, aacdepted Nov. 4, 2003, copyright 3003 Elsevier Inc.
JP 2014-160441, Notification of Reasons for Refusal dated Aug. 18, 2015, 4 pgs.—English, 4 pgs.—Japanese.

* cited by examiner

*Primary Examiner* — Jessica Worsham
(74) *Attorney, Agent, or Firm* — Andrew F. Young, Esq.; Nolte Lackenbach Siegel

(57) ABSTRACT

A starting (raw) material, for cosmetics, comprising a core corona type microgel dispersion obtained by radical polymerization of a specific polyethylene oxide macromonomer, a specific hydrophobic monomer, and a specific cross-linking monomer under specific conditions. The purpose of the present invention is to provide the raw material for cosmetics, with which the cosmetic having a high stability provides a good feeling in use and does not cause skin irritation, can be easily produced.

6 Claims, 1 Drawing Sheet

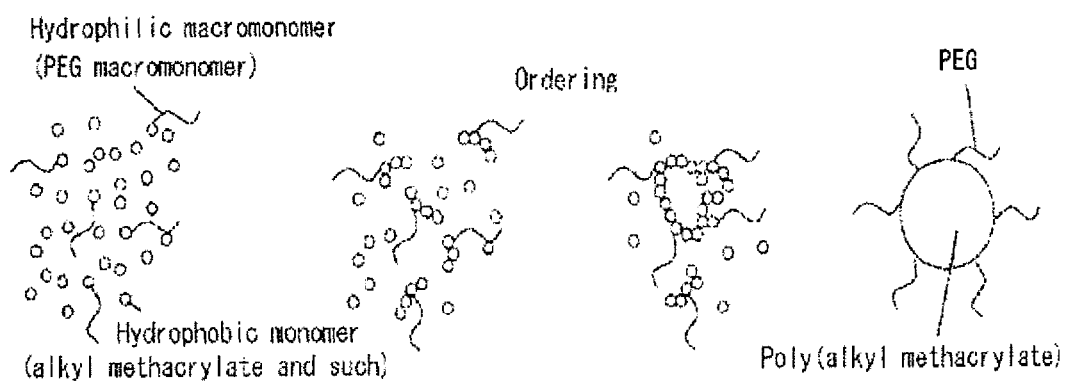

STARTING MATERIAL FOR COSMETICS

RELATED APPLICATIONS

This application relates to and claims priority from PCT Ser. No.: PCT/JP2015/068861 filed Jun. 20, 2015, the entire contents of which are incorporated herein by reference and which in turn claims the priority of Japanese Patent Application No. 2014-160441 filed on Aug. 6, 2014, which is also incorporated herein by reference.

FIELD OF THE INVENTION

The present invention relates to a raw material for cosmetics, and in particular, relates to the raw material for cosmetics that can provide cosmetics with excellent stability and excellent feeling-in-use, and no skin irritation.

BACKGROUND OF THE INVENTION

In order to stably disperse a certain liquid into another liquid, i.e., as a traditional concept of emulsification, it is necessary to add a surfactant (emulsifier). Such emulsifier has an amphiphilic molecular structure that comprise i.e., both polar (hydrophilic) and nonpolar (hydrophobic) moieties in the molecule thereof per se, which are spatially apart each other.

Oil-in-water emulsions used in cosmetics allow aqueous components and oil components to be mixed stably due to the emulsifying effect of the added surfactant. That is, finely dispersed liquid drops of the oil phase are surrounded by shells of the emulsifying agent and the outer phase is the water phase that is the continuous phase; this is said to be the reason for superior feeling in use that gives a dewy freshness.

On the other hand, with the increase in the number of consumers who concern more importance of safety, some of the very sensitive users demand an oil-in-water emulsion that does not have a surfactant that might give irritation or has it in a low enough content to avoid such irritation.

An emulsion prepared by adsorbing powder to the interface, without using a surfactant, is conventionally known as Pickering emulsion.

In the early 1900s, Pickering prepared paraffin/water emulsions that were stabilized by simply adding a colloidal solid such as basic copper sulfate, basic iron sulfate, or metal salts of sulfuric acid. Therefore, this type of emulsion is called a Pickering emulsion. Pickering claimed that the following conditions for the stability of this type of emulsion. (1) The solid particles are suitable for stabilization only when they are significantly smaller than the liquid drops in the inner phase and they don't have a tendency to form aggregates. (2) One of the important properties of the emulsion stabilizing colloidal solid is its wettability. For an O/W emulsion to be stabilized, the colloidal solid must be more wettable with water than, for example, oil.

Pickering emulsions originally surfaced as unwanted secondary effects in a multitude of situations in industrial processes such as the secondary recovery of petroleum, Bitumen extraction from tar sand, and other separation processes involving two types of non-mixing fluids and fine dispersed solid particles. Therefore, the investigation of the corresponding system such as oil/water/soot or oil/water/slate dust system was the original focus of the research.

Pickering emulsions can be seen in various natural and industrial processes such as crude oil recovery, oil separation, cosmetics, and wastewater treatment.

Many research results have been reported on the preparation of Pickering emulsions (Non-Patent Document 1, for example), and its utilization has been proposed in the perfumery and cosmetics field as well (Patent Documents 1 to 3).

However, preparation of an oil-in-water Pickering emulsion that can satisfy temperature stability and stirring stability in various environments, which is essential when applying emulsions for perfumery and cosmetics, has been very difficult. For example, in the case of an oil-in-water Pickering emulsion as described above, powder normally is adsorbed on the interface and stably disperses emulsified particles in the emulsion but, when the emulsion is stirred as it is transported and such, the emulsified particles collide with each other and temporarily transform to expose the interface on which the powder is not adsorbed. The exposed interfaces sometimes coalesce to cause aggregation. Therefore, in terms of emulsification stability, conventional oil-in-water Pickering emulsions can hardly be said to be usable as products such as cosmetics.

Recently it has been disclosed that a stable oil-in-water emulsion composition can be obtained by the combined use of a specific cationic surfactant, polyhydric alcohol, and powder to emulsify the oil phase containing an amphiphilic lipid such as ceramide (see Patent Document 4).

However, Patent Document 4 requires an amphiphilic substance, which forms a liquid crystal structure (a gel) with the surfactant to stabilize the system, but there is a tendency for stickiness at the time of use. Technology to add a very small amount of an amphiphilic substance has been reported (Non-Patent Document 2, for example), but it is difficult to obtain what is sufficiently stable for perfumery and cosmetics; also a new problem arises in terms of the feeling in use such as stickiness of the product due to the amphiphilic substance.

Also, Patent Document 5 discloses that an oil-in-water emulsion that has superior emulsification stability, is free of stickiness and low in irritation can be obtained by adding specific amounts of powder, oil phase components, water phase components, and a cationic surfactant containing two-chain alkyls. In the invention described in Patent Document 5, it is discovered that, by incorporating the cationic surfactant treatment of the powder into the preparation process of the oil-in-water emulsion, said oil-in-water emulsion composition can easily be obtained.

However, the powder used as the emulsifying agent in these Pickering emulsions is mainly inorganic powder (Patent Document 1: polyalkylsilsesquioxane particles, Patent Document 2: metal oxide, Patent Document 3: silica/titanium dioxide/zinc oxide, Patent Document 4: inorganic powder and such, Patent Document 5: hydrophobized fine particle titanium dioxide, red iron oxide, yellow iron oxide, black iron oxide, and aluminum oxide) and the emulsifying ability of these powders is inferior to that of surfactants, therefore the blend ratio has to be higher than that for conventional surfactants.

As a result, squeakiness and powdery sensation from the use of powder and whiteness after the application cannot be avoided, and therefore most of them are inferior in terms of feeling in use.

Patent Document 6 discloses Pickering emulsions using spherical organic particles as the emulsifying agent; but the required blend ratio, combined with elastomer-like organopolysiloxane, is 10% or more and the powdery sensation is not quite reduced.

Patent Document 7 discloses that a hydrophobic monomer emulsion (Pickering emulsion) can be obtained by using hydrophobin as the emulsifying agent. Non-Patent Document 3 reports that a Pickering emulsion can be obtained by using a flavonoid as the emulsifying agent. However, the use of flavonoids and proteins such as hydrophobin raises the concern of allergies and such, and therefore there are many problems in external preparation applications.

As the result of the investigation in view of the above circumstances, a core-corona type microgel can be listed as the emulsifier for an oil-in-water emulsion composition. It is disclosed in Patent Literature 8 that an oil-in-water emulsion composition excellent in emulsion stability, low in a sticky feeling, low in skin irritation, and low in powdery and frictional feelings, due to powder, can be provided by using a core-corona type microgel as the emulsifier. The core-corona type microgel is not only for the emulsifier of an oil-in-water emulsion composition. A clouding agent to provide a white cloudy cosmetic was proposed in Patent Literature 9, and capsule agents based on the swellability with organic solvent are proposed in Patent Literatures 10 and 11.

Methods for preparing a core-corona type microgel are disclosed in Patent Document 8 to 11 and reported in Non-Patent Document 4. All of them are obtained by the radical polymerization of a specific polyethylene oxide macromonomer, a specific hydrophobic monomer, and a specific cross-linking monomer in a water-ethanol mixed solvent. The dispersion liquid is replaced with water by dialyzing the obtained polymer solution against water.

However, in view of the application of a core-corona type microgel as an emulsifier, clouding agent, or capsule agent, the purification process by dialysis is not industrially suitable. In the process of removing the solvent by heating, evaporation, etc., the aggregation/fusion of polymer fine particles of the core-corona type microgel becomes a concern, and it is not suitable at the industrial mass production level.

Therefore, the obtained polymer solution as it is may be considered to be used as the raw material body. In the polymer solution, a polymerized core-corona type microgel, residual monomers, and the polymerization solvent are contained; if polymerization conditions are sufficiently optimized and the amount of the residual monomers can be reduced, it can be used as it is as the raw material body.

However, as described above, the polymerization solvent for a core-corona type microgel is usually a water-ethanol mixed solvent. When the polymer solution is used as it is as the raw material body, a high concentration of ethanol is always contained in the raw material body. As a result, ethanol is also contained in the oil-in-water emulsion composition and in white cloudy cosmetics when this is blended as the raw material.

Ethanol is frequently used as a solvent that provides various effects of such as cleaning, disinfection, astringency, and solubility on cosmetics. On the other hand, an excessive response is induced on the skin depending upon the blending concentration and composition, and ethanol sometimes becomes the cause of redness, itching, a burning sensation, etc. Ethanol-free formulations shown in terms of "alcohol-free" or "non-alcohol" may be provided to the consumers with the skin that overreacts to such irritation (sensitive skin). However, when ethanol is contained in the raw materials, such formulations cannot be produced.

Patent Document 1: Japanese patent publication No. 2656226
Patent Document 2: International unexamined patent publication No. 2001-518111
Patent Document 3: International unexamined patent publication No. 2007-332037
Patent Document 4: Japanese unexamined patent publication No. 2006-36763
Patent Document 5: Japanese unexamined patent publication No. 2008-291026
Patent Document 6: International unexamined patent publication No. H11-158030
Patent Document 7: International unexamined patent publication No. 2009-501256
Patent Document 8: Japanese patent publication No. 5207424
Patent Document 9: Japanese patent publication No. 4577721
Patent Document 10: International unexamined patent publication No. 2006-161026
Patent Document 11: International unexamined patent publication No. 2006-161027
Non-Patent Document 1: Binks et. al, Advances in Colloid and Interface Science, 100-102 (2003).
Non-Patent Document 2: Mukul M, Sharma et. al, Journal of Colloid and Interface Science, 157, 244-253 (1993).
Non-Patent Document 3: J. Agric. Food Chem., 59, 263-2645 (2011).
Non-Patent Document 4: J. Colloid Interface Sci., 274, 49 (2004).

DISCLOSURE OF THE INVENTION

Problem to be Solved by the Invention

The present invention was made in view of the above-described conventional art. An object of the invention is to develop a production method of raw material for cosmetics and to provide an oil-in-water emulsion cosmetic and a white cloudy cosmetic that is without skin irritation, excellent in stability, and low in thickening feeling and powdery sensation.

Means to Solve the Problem

That is, the raw material for cosmetics of the present invention is characterized by comprising a core-corona type microgel dispersion liquid characteristically obtained by polymerizing polyethylene oxide macromonomers of the following chemical formula (1), hydrophobic monomers of the following chemical formula (2), and cross-linking monomers of the following chemical formula (3) under the following conditions (A) to (E).

(A) the mole ratio of the feed mole amount of said polyethylene oxide versus the feed mole amount of the hydrophobic monomers is in a range of 1/1 to 10/250, (B) the feed amount of the cross-linking monomers is 0.1 to 1.5% by mass relative to the feed amount of the hydrophobic monomers, (C) the hydrophobic monomer represented by the following chemical formula (2) is a monomer composition, wherein one or more selected from methacrylic acid derivatives having alkyl groups having 1 to 8 carbon atoms are mixed, (D) the polymerization solvent is a water-polyol mixed solvent, and the polyol is one or more selected from the group consisting of dipropylene glycol, 1,3-butylene glycol, and isoprene glycol, and (E) the solvent composition of the water-polyol mixed solvent is water/polyol=a range of 90/10 to 10/90 (mass/mass) at 20° C.

[Chemical Formula 1]

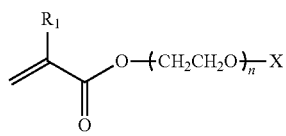

$R_1$ is s an alkyl group having 1 to 3 carbon atoms, and n is a number of 8 to 200. X is H or $CH_3$.

[Chemical Formula 2]

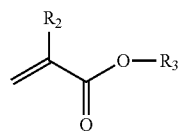

$R_2$ is an alkyl group having 1 to 3 carbon atoms, and $R_3$ is an alkyl group having 1 to 12 carbon atoms.

[Chemical Formula 3]

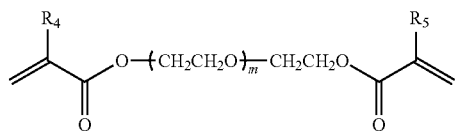

$R_4$ and $R_5$ are independent alkyl groups having 1 to 3 carbon atoms, and m is a number of 0 to 2.

In the above raw material for cosmetics, it is preferable that the raw material for cosmetics does not contain ethanol.

The emulsifier of the present invention is characterized by consisting of the above raw material for cosmetics.

The clouding agent is characterized by consisting of the above raw material for cosmetics.

The oil-in-water emulsion cosmetic, comprising (a) the above emulsifier, (b) oil phase components, and (e) aqueous phase components of the present invention, is characterized by containing, as (b) the oil phase components, one or more oil phase components selected from the group consisting of hydrocarbon oils, higher fatty acids, higher alcohols, synthetic ester oils, silicone oils, liquid oils and fats, solid oils and fats, waxes, and perfumes, and is emulsified with (a) the emulsifier.

In the above oil-in-water emulsion cosmetic, it is preferable that the oil-in-water emulsion cosmetic does not contain ethanol.

The white cloudy cosmetic of the present invention is characterized by comprising the above clouding agent.

In the above white cloudy cosmetic, it is preferable that the white cloudy cosmetic does not contain ethanol.

Effect of the Invention

The present invention provides a raw material for cosmetics with which oil-in-water emulsion cosmetics and white cloudy cosmetics that are excellent in stability and the feeling in use and have no skin irritation can easily be obtained.

(1) The raw material for cosmetics obtained by the production method of the present invention can be blended, without purification, into the cosmetics targeted for all skin types. In particular, when blended in sensitive-skin type cosmetics, cosmetics without skin irritation can easily be obtained.

(2) The oil-in-water emulsion cosmetic blending the raw material for cosmetics of the present invention as an emulsifier has superior emulsification properties. Even if the blending quantity of the raw material for cosmetics is small, good oil-in-water emulsion compositions can be obtained. Also, even if the ratio of the oil phase components/water phase components is high (the amount of the oil phase components is large), a good oil-in-water emulsion composition can be obtained.

(3) The oil-in-water emulsion cosmetic blending the raw material for cosmetics of the present invention as an emulsifier has superior emulsification stability. Unlike conventional Pickering emulsions, the emulsified state is not damaged by stirring or vibration, and the temperature stability is also good because there is little change in the physical properties of the surfactant due to temperature just like emulsions obtained by using a conventional surfactant.

(4) The oil-in-water emulsion cosmetic blending the raw material for cosmetics of the present invention as an emulsifier has superior feeling in use. Powdery sensation and squeakiness due to the use of powder, which is seen with conventional Pickering emulsions, are reduced and there is no stickiness due to the surfactant, which is seen with emulsions obtained by using a conventional surfactant.

(5) Cosmetics in which the raw material for cosmetics of the present invention is blended as the clouding agent are excellent in white turbidity. Even when the blending quantity of the clouding agent is small, good white turbidity can be obtained.

(6) Cosmetics in which the raw material for cosmetics of the present invention is blended as the clouding agent are excellent in storage stability. That is, the white turbidity is stable after long-term storage.

(7) Cosmetics in which the raw material for cosmetics of the present invention is blended as the clouding agent are excellent in feeling in use. That is, there is a full-bodied feeling without stickiness. In addition, the blending is fast, and when applied on the skin, there is an effect to suppress undesired shine.

BRIEF DESCRIPTION OF THE DRAWINGS

FIG. 1 is an illustration showing the mechanism of generation of the microgel in the raw material for cosmetics of the present invention.

BEST MODE FOR CARRYING OUT THE INVENTION (a) Raw Material for Cosmetics)

The raw material for cosmetics of the present invention is a core-corona type microgel dispersion obtained by the radical polymerization, under specific conditions, of the monomers represented by below chemical formulas (1) to (3).

For the polyethylene oxide macromonomers of chemical formula (1), commercial products commercially available from Aldrich or BLEMMER (registered trademark) sold by NOF Corporation can be used.

The molecular weight (i.e. the value of n) of the polyethylene oxide part is in the range of n=8 to 200.

Such examples of macromonomers include BLEMMER (registered trademark) PME-400, BLEMMER (registered trademark) PME-1000, and BLEMMER (registered trademark) PME-4000 from NOF Corporation.

[Chemical Formula 1]

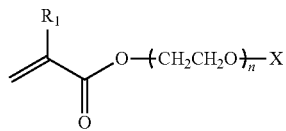

(1)

$R_1$ is an alkyl group having 1 to 3 carbon atoms, and n is a number of 8 to 200. X is H or $CH_3$.

For the hydrophobic monomer of chemical formula (2), commercial products are commercially available from Aldrich or Tokyo Chemical Industry Co., Ltd.

[Chemical Formula 2]

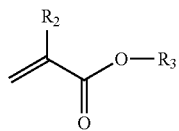

(2)

$R_2$ is an alkyl group having 1 to 3 carbon atoms. $R_3$ is an alkyl group having 1 to 12 carbon atoms and more preferably the alkyl group having 1 to 8 carbon atoms.

As examples of hydrophobic monomers, methyl acrylate, ethyl acrylate, propyl acrylate, butyl acrylate, pentyl acrylate, hexyl acrylate, heptyl acrylate, octyl acrylate, decyl acrylate, dodecyl acrylate, methyl methacrylate, ethyl methacrylate, propyl methacrylate, butyl methacrylate, pentyl methacrylate, hexyl methacrylate, heptyl methacrylate, octyl methacrylate, decyl methacrylate, and dodecyl methacrylate. Particularly preferable are methyl methacrylate, butyl methacrylate, and octyl methacrylate are preferably used.

These hydrophobic monomers are commodity raw materials and they can also be obtained easily as general industrial raw materials.

The cross-linking monomer of chemical formula (3) can be obtained as a commercially available product or an industrial raw material. This cross-linking monomer is preferably hydrophobic.

A value range of m is preferably 0 to 2. Specific preferable examples include ethylene glycol dimethacrylate (hereafter sometimes abbreviated as EGDMA) sold by Aldrich and BLEMMER PDE-50 (registered trademark) sold by NOF Corporation.

[Chemical Formula 3]

(3)

$R_4$ and $R_5$ are independent alkyl groups having 1 to 3 carbon atoms, and m is a number of 0 to 2.

The core-corona type microgel dispersion liquid, which is a raw material for cosmetics of the present invention, is prepared by copolymerizing the aforementioned monomers under the following conditions (A) to (E) with radical polymerization method.

(A) the mole ratio of the feed mole amount of said polyethylene oxide/feed mole amount of the hydrophobic monomers is in a range of 1:10 to 1:250, (B) the feed amount of said cross-linking monomers is 0.1 to 1.5% by mass relative to the feed amount of said hydrophobic monomers, (C) the hydrophobic monomer represented by the following chemical formula (2) is a monomer composition, wherein one or more selected from methacrylic acid derivatives having alkyl groups of 1 to 8 carbon atoms are mixed, (D) the polymerization solvent is a water-polyol mixed solvent, and the polyol is one or more selected from the group consisting of dipropylene glycol, 1,3-butylene glycol, and isoprene glycol, and (E) the solvent composition of the water-polyol mixed solvent is water/polyol=a range of 90/10 to 10/90 (mass/mass) at 20° C.

In the present invention, "the feed amount of said cross-linking monomer over the feed amount of said hydrophobic monomer" is defined as the cross-link density (% by mass). Due to condition (B), the cross-link density of the core-corona type microgel used in the present invention, as defined as the feed amount of said cross-linking monomers relative to the feed amount of said hydrophobic monomers, must be 0.1 to 1.5% by mass.

(Condition (A))

For the mole quantity of the polyethylene oxide macromonomer and the hydrophobic monomer, it can be polymerized when the mole ratio of the feed mole amount of said polyethylene oxide/feed mole amount of the hydrophobic monomers is in the range of 1:10 to 1:250 (mole ratio) as specified in condition (A). The feed mole amount is preferably in a range of 1:10 to 1:200 and more preferably in a range of 1:25 to 1:100.

When the mole amount of the hydrophobic monomer is 10 times or less of that of the polyethylene oxide macromonomer, the polymerized polymer becomes water soluble and does not form a core-corona type microgel. In addition, when the mole amount of the hydrophobic monomer is 250 times or more of that of the polyethylene oxide macromonomer, the dispersion stabilization by the polyethylene oxide macromonomer becomes insufficient, so that the hydrophobic polymer due to the insoluble hydrophobic monomer may aggregate and precipitate.

(Condition (B))

A microgel of which core part has a cross-linking hydrophobic polymer can be polymerized by polymerizing cross-linking monomer.

When the feed amount of the cross-linking monomer is less than 0.1% by mass relative to the feed amount of the hydrophobic monomer, the cross-link density is low and this microgel breaks down when swollen. When it is over 1.5% by mass, aggregation of microgel particles occurs and it is impossible to polymerize preferable microgel particles having a narrow particle size distribution. The feed amount of the cross-linking monomer is preferably in a range of 0.2 to 1.0% by mass, more preferably 0.2 to 0.8% by mass, most preferably 0.2 to 0.5% by mass.

(Condition (C))

The hydrophobic monomers of chemical formula (2) preferably have a monomer composition of a mixture of one or more methacrylic acid derivatives that have an alkyl having 1 to 8 carbon atoms. When the number of carbon atoms is 0 (when the monomer does not have an end ester bond), the monomers may be too hydrophilic for good emulsification polymerization. On the other hand, when the number of carbon atoms is 9 or more, then steric hindrance occurs during the polymerization and the cross-linking structure may not be formed well.

(Condition (D))

It is necessary that the polymerization solvent is a water-polyol mixed solvent. The preferable polyol is the one that can dissolve a hydrophobic monomer represented by chemical formula (2) and a cross-linking monomer represented by chemical formula (3). It is necessary that dipropylene glycol, 1,3-buthylene glycol, and isoprene glycol are used in the present invention.

Under consideration of that when the polymer solution as-is is used far is the raw material applicable to an industrial production without further purification process such as dialysis, the solvent to be mixed with water should not be an organic solvent such as ethanol, propanol, or butanol, because such solvents may cause irritation when applied on the skin; so that polyol that is generally blendable into cosmetics is inevitable.

(Condition (E))

It is necessary that the solvent composition of the water-polyol mixed solvent, used as the polymerization solvent, is water/polyol=a range of 90/10 to 10/90 in the mass ratio at 20° C. The solvent composition of the water-polyol mixed solvent, used as the polymerization solvent, is preferably water/polyol=a range of 90/10 to 10/90 (% by mass at 20° C.) and more preferably water/polyol=a range of 80/20 to 20/80 (% by mass at 20° C.).

For the polymerization solvent, it is necessary to add polyol for homogeneous dissolution of the hydrophobic monomer. The mix ratio of polyol is 10 to 90 (mass/mass). When the mix mass of polyol is lower than 10% by mass, the dissolution of the hydrophobic monomer becomes extremely poor, and polymerization proceeds in the state in which the monomer is as droplets, so that gigantic masses can be formed but no microgel can be formed. When the mix mass of polyol exceeds 90% by mass, an emulsion of the hydrophobic monomer cannot be formed by hydrophobic interaction, so that no emulsion polymerization can proceed and no microgel can be obtained.

The thus obtained raw material for cosmetics of the present invention does not contain ethanol because the polymerization solvent is water-polyol mixed solvent. By using the raw material which does not contain ethanol according to the present invention, cosmetics without skin irritation to the users with sensitive skin can be easily obtained.

The use of polyols, which are widely-used cosmetic raw material, as the polymerization solvent is not common, and it is limited to very a special application such as "to allow the polymerization solvent to remain as it is as a raw material body" of the present invention. As the polymerization solvent, those with a high solubility of monomers are often selected; however, many of the polyols for cosmetics are poor in this respect. In addition, many of the polyols have high viscosity and a high boiling point, so that they are not suitable in view of the conventional production and purification processes (distillation etc.).

However, as a result of the investigation of various solvents by the present inventors, a polyol selected from the group consisting of dipropylene glycol, 1,3-butylene glycol, and isoprene glycol was found to be suitable as the polymerization solvent.

For the polymerization initiator for use in this polymerization system, commercially available polymerization initiators used for water soluble thermal radical polymerization can be used. With this polymerization system, polymerized microgel particles in a very narrow particle size distribution can be obtained without accurately controlling the stirring conditions.

Microgels from conventional synthetic polymers all use polymer electrolytes, polyacrylic acid for example, of which dispersibility in water lacks acid resistance and/or salt resistance. However, when considering applications as components for medical drugs and/or cosmetics, acid resistance and/or salt resistance are very important features to adapt to physiological conditions. The raw material for cosmetics of the present invention is a microgel stabilized by polyethylene oxide chains, which are a nonionic polymer, and its dispersion stability in water can be expected to have acid resistance and/or salt resistance.

The polymer fine particle polymerization method by the macromonomer method using macromonomers containing a water soluble polymer structure is known, but a method that uses this method to cross-link the core part with cross-linking monomers to prepare a microgel is not known.

In the microgel used in the present invention, it is believed that the hydrophilic macromonomer and the hydrophobic monomer are ordered in the solvent as shown in FIG. 1 and a core-corona type microgel having an almost constant particle size and a cross-linking core part is generated.

The raw material for cosmetics can be blended in cosmetic as a cloudy agent. White turbidity can visually be confirmed by blending only 0.01% (net) of the raw material for cosmetics of the present invention into water. By blending 0.01 to 0.1% thereof the white turbidity with the L value (brightness) of 1 to 80, measured with a Macbeth color difference meter, can be obtained.

In the present invention, a white cloudy cosmetic means a cosmetic of which appearance can be visually recognized as turbid. L value is preferably 1 to 90.

The adjustment of the surfactant and oil balance in the white cloudy cosmetic was very difficult by the conventional technology, and the production of a stable white cloudy cosmetic was difficult. In addition, surfactants and oils with which a white cloudy cosmetic can be prepared are limited; as a result, it was difficult to obtain a white cloudy cosmetic excellent in the feeling in use.

In the case that the raw material for cosmetics of the present invention is blended in cosmetics such as a white cloudy cosmetic, they are produced by mixing and dispersing the raw material for cosmetics into water (or an aqueous phase in which aqueous components are dissolved) by the conventional method.

It is preferable that the blending quantity of the raw material for cosmetics of the present invention in a cosmetic is normally 0.01 to 10 mass % (net; hereinafter, expressed simply by %) with respect to the total amount of the cosmetic. When the blending quantity of the microgel is less than 0.01% (net), it is difficult to obtain a stable cosmetic. When the blending quantity exceeds 10% (net), it may not be preferable as a cosmetic in terms of stability during long term storage at high temperatures and the feeling in use may be poor.

The raw material for cosmetics of the present invention can be blended into cosmetics as an excellent Pickering emulsion emulsifier.

That is, the raw material for cosmetics of the present invention forms oil-in-water emulsion cosmetics that have a structure wherein a core-corona type microgel emulsifier is adsorbed on the oil droplets of the oil phase components. The oil droplets are dispersed in the aqueous phase components after the emulsification of the oil phase components and the aqueous phase components. Accordingly, the core-corona type microgel emulsifier of the present invention is excellent in emulsifying capability. When the raw material for cosmetics of the present invention is used as an emulsifier, oil-in-water emulsion cosmetics excellent in emulsion stability can be produced.

The oil-in-water emulsion cosmetics of the present invention are produced by mixing and dispersing the raw material for cosmetics in water or aqueous phase components, adding the oil phase components and other components, and emulsifying them by stirring and applying a shearing force by the conventional method.

In the case that the raw material for cosmetics of the present invention is blended in the oil-in-water emulsion cosmetics, they are produced by mixing and dispersing (a) the raw material for cosmetics in (c) the water or aqueous phase components, adding (b) the oil phase components and other components, and emulsifying by stirring and applying a shearing force by the conventional method. That is, the raw material for cosmetics of the present invention has excellent commercial value in that oil-in-water emulsion cosmetics without ethanol can be produced by a very simple production process.

((b) Oil Phase Component)

Examples of the oil phase components include hydrocarbon oils, higher fatty acids, higher alcohols, synthetic esters, silicone oils, liquid fats and oils, solid fats and oils, waxes, and fragrances that are commonly used in cosmetics, quasi-drugs, etc.

Examples of the hydrocarbon oils include isododecane, isohexadecane, isoparaffin, liquid petrolatum, ozocerite, squalane, pristane, paraffin, ceresin, squalene, petrolatum, and microcrystallin wax.

Examples of the higher fatty acids include lauric acid, myristic acid, palmitic acid, stearic acid, behenic acid, oleic acid, undecylenic acid, tall oil, isostearic acid, linolic acid, linoleic acid, eicosapentaenoic acid (EPA), and docosahexaenoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain alcohols (for example, monostearyl glycerin ether (batyl alcohol), 2-decyltetradecynol, lanolin alcohol, cholesterol, phytosterol, hexyl dodecanol, isostearyl alcohol, and octyl dodecanol).

Examples of the synthetic ester oils include octyl octanoate, nonyl nonanoate, cetyl octanoate, isopropyl myristate, octyl dodecyl myristate, isopropyl palmitate, butyl stearate, hexyl laurate, myristyl myristate, decyl oleate, hexyl decyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, n-alkylene glycol monoisostearate, neopentyl glycol dicaprate, tripropylene glycol pivalate, diisostearyl malate, glyceryl di-2-heptylundecanoate, glyceryl diisostearate, trimethylolpropane tri-2-ethyl hexanoate, trimethylolpropane triisostearate, pentaerythritol tetra-2-ethylhexanoate, glycerin tri-2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, castor oil fatty acid methyl ester, oleyl oleate, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane), ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, various modified polysiloxanes (amino-modified polysiloxane, polyether-modified polysiloxane, alkyl-modified polysiloxane, and fluorine-modified polysiloxane), and acryl silicones.

Examples of the liquid fats and oils include avocado oil, tsubaki oil, turtle fatty acid, macadamia nut oil, corn oil, mink oil, olive oil, rapeseed oil, egg yolk oil, sesame oil, persic oil, wheat germ oil, sasanquan oil, castor oil, linseed oil, safflower oil, cotton seed oil, perilla oil, soybean oil, peanut oil, tea seed oil, Japanese nutmeg oil, rice bran oil, Chinese gimlet oil, Japanese gimlet oil, jojoba oil, germ oil, and triglycerin.

Examples of the solid fats and oils include cacao butter, coconut oil, horse fat, hydrogenated coconut oil, palm oil, beef tallow, mutton tallow, hydrogenated beef tallow, palm kernel oil, lard, beef bone fat, Japanese core wax nucleus oil, hydrogenated oil, neatsfoot oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Selection of the perfume is not limited in particular; examples include natural perfumes from animals or plants, synthetic perfumes prepared by means of chemical synthesis, and perfume blends thereof. By blending perfume, a cosmetic having a superior durability of fragrance can be obtained.

Specific examples of perfumes include acetivenol, anise aldehyde, anethole, amyl acetate, amyl salicylate, allyl amyl glycolate, allyl caproate, aldehyde C6-20, ambrettolide, ambrettolide, ambroxan, ionone, Iso E Super, eugenol, auranthiol, galaxolide, calone, coumarin, geraniol, geranyl acetate, Sandalore, santalol, sandela, cyclamen aldehyde, cis-3-hexenyl acetate, cis-3-hexenol, citral, citronellyl acetate, citronellol, cineole, dihydromyrcenol, jasmolactone, cinnamic alcohol, cinnamic aldehyde, styralyll acetate, cedryl acetate, cedrol, damascone, damascenone, decalactone, terpinyl acetate, terpineol, tonalid, tonalide, triplal, nerol, bacdanol, vanillin, hydroxycitronellal, phenylethyl acetate, phenylethyl alcohol, hexyl salicylate, vetiveryl acetate, hedione, heliotropin, helional, vertofix, benzyl acetate, benzyl salicylate, benzyl benzoate, pentalide, pentalide, bornyl acetate, myol, musk ketone, methyl anthranilate, methyl dihydrojasmonate, yara yara, lime oxide, linalyl acetate, linarol, limonene, Lyral, lilial, rose oxide, rhodinol, Angelica oil, anise oil, Artemisia vulgaris oil, basil oil, bay oil, Bergamot oil, calamus oil, camphor oil, cananga oil, cardamom oil, cassia oil, cedar wood oil, celery oil, chamomile oil, cinnamon oil, clove oil, coriander oil, cumin oil, dill oil, elemi oil, estragon oil, eucalyptus oil, fennel oil, fenugreek oil, galbanum oil, geranium oil, ginger oil, grapefruit oil, gaiac wood oil, cypress leaf oil, cypress oil, juniper berry oil, lavandin oil, lavender oil, lemon oil, lime oil, mandarin oil, ziram oil, mimosa oil, peppermint oil, spearmint oil, mill oil, myrtle oil, nutmeg oil, oakmoss oil, olibanum oil, opoponax oil, orange oil, parsley oil, patchouli oil, pepper oil, perilla oil, petit grain oil, neroli oil, orange flower, oil, pimento oil, all spice oil, pine oil, rose oil, rosemary oil, clary sage oil, sage oil, sandalwood oil, styrax oil, taget oil, thyme oil, tuberose oil, valerian oil, vetiver oil, violet leaf oil, wintergreen oil, wormwood oil, ilan ilan oil, yuzu oil, cassie absolute, genet absolute, hyacinth absolute, immortelle absolute, jasmine absolute, jonquil absolute, narcis absolute, rose absolute, violet leaf absolute, and benzoin.

In the case of conventional emulsion compositions obtained by surfactants, the physical properties of the surfactant and the physical properties of the oil component significantly influence emulsifiability, and changes in the oil component required changes in the types of the surfactant. However, since the oil-in-water emulsion composition of the present invention is a Pickering emulsion using (a) microgel for the emulsifying agent, the type of the oil component does not greatly influence emulsifiability, stability and such and therefore a wider range of types of the oil component can be blended in.

((c) Water Phase Component)

Water, water soluble alcohols, thickeners, etc. commonly used in cosmetics, quasi-drugs, etc. can be blended as water phase component; in addition, appropriate amounts of moisturizers, chelating agents, preservatives, pigments, etc. can also be blended in as desired.

The selection of water contained in the oil-in-water emulsion composition of the present invention is not limited in particular; specific examples include purified water, ion-exchanged water, and tap water.

Examples of water soluble alcohols include lower alcohols, polyhydric alcohols, polyhydric alcohol polymers, dihydric alcohol alkyl ethers, dihydric alcohol ether esters, glycerin monoalkyl ethers, sugar alcohols, monosaccharides, oligosaccharides, polysaccharides, and derivatives thereof.

Examples of lower alcohols include ethanol, propanol, isopropanol, isobutyl alcohol, and t-butyl alcohol.

However, ethanol may cause skin irritation to the sensitive skin. Thus, in the oil-in-water emulsion cosmetic or white cloudy cosmetic of the present invention, the blending quantity of ethanol is preferably 0.3% by mass or less and more preferably 0% by mass with respect to the total cosmetic. Cosmetics without skin irritation to the users with sensitive skin can be obtained by not blending ethanol.

Examples of polyhydric alcohols include: dihydric alcohols (for example, dipropylene glycol, 1,3-butylene glycol, ethylene glycol, trimethylene glycol, 1,2-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, diglycerin and pentaerythritol such as 1,2,6-hexanetriol); pentahydric alcohols (for example, xylitol and triglycerin); hexahydric alcohols (for example, sorbitol and mannitol); polyhydric alcohol polymers (for example, diethylene glycol, dipropylene glycol, triethylene glycol, polypropylene glycol, tetraethylene glycol, diglycerin, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin mono alkyl ethers (for example, xylyl alcohol, selachyl alcohol, and batyl alcohol); sugar alcohols (for example, maltotriose, mannitol, sucrose, erythritol, glucose, fructose, starch amylolysis sugar, maltose, and alcohol prepared by the reduction of starch amylolysis sugar); glysolid; tetrahydro furfuryl alcohol; POE-tetrahydro furfuryl alcohol; POP-butyl ether; POP/POE-butyl ether; tripolyoxypropylene glycerin ether; POP-glycerin ether; POP-glycerin ether phosphoric acid; POP/POE-pentane erythritol ether; and polyglycerin.

Examples of monosaccharides include: trioses (for example, D-glyceryl aldehyde and dihydroxyacetone); tetroses (for example, D-etythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose); deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and morainic acid); and uronic acid (for example, D-glucuronic acid, D-mannuronic acid, L-guluronic acid, D-galacturonic acid, and L-iduronic acid).

Examples of oligosaccharides include sucrose, gentianose, umbelliferose, lactose, planteose, isolignoses, α, α-trehalose, raffinose, lignoses, umbilicine, stachyose and verbascoses.

Examples of polysaccharides include cellulose, quince seed, starch, galactan, dermatan sulfate, glycogen, gum arabic, heparan sulfate, traganth gum, keratan sulfate, chondroitin, xanthan gum, guar gum, dextran, kerato sulfate, locust bean gum, and succinoglucan.

Examples of polyols include polyoxyethylene methyl glucoside (Glucam E-10) and polyoxypropylene methyl glucoside (Glucam P-10).

Examples of thickeners include: gum arabic, carrageenan, karaya gum, gum tragacanth, carob gum, quince seed (*Cydonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of natural water-soluble polymers include: plant-type polymers (for example, gum arabic, gum tragacanth, galactan, guar gum, carob gum, karaya gum, carrageenan, pectin, agar, quince seed (*Cydonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

Examples of semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymetyl-cellulose, sodium carboxymethyl cellulose, crystal cellulose, and cellulose powder); and alginic acid-type polymers (for example, sodium alginate and propylene glycol alginate).

Examples of synthetic water-soluble polymers include: vinyl polymers (for example, polyvinyl alcohol, polyvinyl methyl ether, polyvinylpyrrolidone, carboxy vinyl polymer); polyoxyethylene-type polymers (for example, polyethylene glycol 20,000, 40,000, 60,000, etc.); acrylic polymers (for example, sodium polyacrylate, polyethylacrylate, and polyacrylamide); polyethyleneimine; and cationic polymers.

Examples of moisturizers include chondroitin sulfate, hyaluronic acid, rnucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, chestnut rose fruit extract, yarrow extract, and sweet clover extract.

Examples of sequestering agents include 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

Examples of amino acids include neutral amino acids (for example, threonine and cysteine) and basic amino acids (for example, hydroxylysine). Examples of the amino acid derivatives include sodium acyl sarcosinate (sodium N-lauroyl sarcosinate), acyl glutamate, sodium acyl β-alanine, and glutathione.

Examples of pH adjustment agents include buffers such as lactic acid-sodium lactate, citric acid-sodium citrate, and succinic acid-sodium succinate.

The blend quantity of the oil phase components and the water phase components in the oil-in-water emulsion composition of the present invention are not prescribed in particular. By using (a) raw material for cosmetics as an emulsifier, an oil-in-water emulsion composition with a wide range of oil phase components/water phase components ratios, ranging from embodiments having smaller oil phase components/water phase components ratios, i.e., smaller blend ratios of the oil phase components (essences, emulsions, etc.) to embodiments having larger blend ratios of the oil phase components (cleansing creams, sunscreens, hair creams, etc.) can be obtained.

Other components normally used in external preparations such as cosmetics and quasi-drugs can be blended as necessary in the cosmetic of the present invention as long as the effect of the present invention is not adversely affected; examples of such components include ultraviolet absorbents, powders, organic amines, polymer emulsions, vitamins, and antioxidants.

Examples of water soluble ultraviolet absorbents include benzophenone-type ultraviolet absorbents such as 2,4-dihydroxybenzophenone, 2,2'-dihydroxy-4-methoxy benzophenone, 2,2'-dihydroxy-4,4'-dimethoxybenzophenone, 2,2',4,4'-tetrahydroxy benzophenone, 2-hydroxy-4-methoxy benzophenone, 2-hydroxy-4-methoxy-4'-methylbenzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone, and 4-hydroxy-3-carboxy benzophenone, the benzimidazole-type ultraviolet absorbent such as phenylbenzimidazole-5-sulfonic acid and salts thereof and phenylene-bis-benzimidazole-tetrasulfonic acid and salts thereof, as well as 3-(4'-methylbenzylidene)-d,l-camphor, 3-benzylidene-d,l-camphor, urocanic acid, and urocanic acid ethyl ester.

Examples of the oil soluble ultraviolet absorbents include: benzoic acid-type ultraviolet light absorbents such as paraminobenzoic acid (PABA), PABA monoglycerin ester, N, N-dipropoxy PABA ethyl ester, N, N-diethoxy PABA ethyl ester, N,N-dimethyl PABA ethyl ester, and N, N-dimethyl PABA butyl ester; anthranilic acid-type ultraviolet light absorbents such as homo mentyl-N-acetyl anthranilate; salicylic acid-type ultraviolet light absorbents such as amyl salicylate, mentyl salicylate, homo mentyl salicylate, octyl salicylate, phenyl salicylate, benzyl salicylate, and p-isopropanol phenyl salicylate; cinnamic acid-type ultraviolet absorbents such as octyl cinnamate, ethyl-4-isopropyl cinnamate, methyl-2,5-diisopropyl cinnamate, ethyl-2,4-diisopropyl cinnamate, methyl-2,4-di isopropyl cinnamate, propyl-p-methoxy cinnamate, isopropyl-p-methoxy cinnamate, isoamyl-p-methoxy cinnamate, octyl-p-methoxy cinnamate, 2-ethylhexyl-p-methoxy cinnamate, 2-ethoxyethyl-p-methoxy cinnamate, cyclohexyl-p-methoxy cinnamate, ethyl-α-cyano-.beta.-phenyl cinnamate, 2-ethylhexyl-α, α-cyano-β-phenyl cinnamate, glyceryl mono-2-ethyl hexanoyl-diparamethoxy cinnamate, and 3-methyl-4-[methylbis(trimethylsiloxy)silyl]butyl 3,4,5-trimethoxy cinnamate; 2-phenyl-5-methyl benzoxazole, 2,2'-hydroxy-5-methylphenyl benzotriazol, 2-(2'-hydroxy-5'-t-octylphenyl) benzotriazol, 2-(2'-hydroxy-5'-methylphenyl)benzotriazol, dibenzaladine, dianisoylmethane, 4-methoxy-4'-t-butyl dibenzoyl-methane, and 5-(3,3'-dimethyl-2-norbornylidene)-3-pentane-2-one, and octocrylene.

Examples of powder components include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, zinc myristate, calcium palmitate, and aluminum stearate), and boron nitride); organic powders (for example, polyamide resin powder (nylon powder), polyethylene powder, poly-methyl methacrylate powder, polystyrene powder, powders of the copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, .gamma.-iron oxide); inorganic yellow pigments (for example, yellow iron oxide and loess); inorganic black pigments (for example, black iron oxide and low oxides of titanium); inorganic purple pigments (for example, mango violet, cobalt violet); inorganic green pigments (for example, chromium oxide, chromium hydroxide, and cobalt titanate); inorganic blue pigments (for example, ultramarine blue and Berlin blue); pearl pigment (for example, titanium oxide coated mica, titanium oxide coated bismuth oxychloride, titanium oxide coated talc, coloration titanium oxide coated mica, bismuth oxychloride, fish scale flakes); metal powder pigments (for example, aluminum powder, copper powder); organic pigments such as zirconium, barium or aluminum rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1); and natural colors (for example, chlorophyll and .beta.-carotene).

Examples of organic amines include monoethanolamine, diethanolamine, triethanolamine, morpholine, tetrakis(2-hydroxypropyl)ethylenediamine, tri isopropanolamine, 2-amino-2-methyl-1,3-propanediol, and 2-amino-2-methyl-1-propanol.

Examples of polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of vitamins include vitamins A, B1, B2, B6, C and E as well as their derivatives, pantothenic acid and its derivatives, and biotin.

Examples of antioxidants include tocopherols, dibutyl hydroxytoluene, butyl hydroxyanisole, and gallic acid ester.

Examples of antioxidation assistants include phosphoric acid, citric acid, ascorbic acid, maleic acid, malonic acid, succinic acid, fumaric acid, cephalin, hexametaphosphate, phytic acid, and ethylene diamine tetraacetic acid.

Examples of other possible components include antiseptics (methylparaben, ethylparaben, butylparaben, and phenoxyethanol); antiphlogistic agents (for example, glycyrrhizic acid derivatives, glycyrrhetinic acid derivatives, salicylic acid derivatives, hinokitiol, zinc oxide, and allantoin); whitening agents (for example, placenta extract, creeping saxifrage extract, and arbutin); various extracts (for example, Phellodendri Cortex, goldthread, *Lithospermum* root, *Paeonia lactiflora, Swertia japonica*, Birch, sage, loquat, carrot, aloe, *Malva sylvestris*, Iris, grape, Coix mayuen, sponge gourd, lily, saffron, *Cnidium officinale*, sheng jiang, *Hypericum erectum*, Ononis, garlic, Guinea pepper, chen pi, *Ligusticum acutilobum*, and seaweed), activators (royal jelly, photosensitive substances, and cholesterol derivatives); blood circulation promoting agents (for example, nonyl acid valenyl amide, nicotinic acid benzyl esters, nicotinic acid .beta.-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and .gamma.-orizanol); anti-seborrhea agents (for example, sulfur and thiantol); and anti-inflammatory agents (for example, tranexamic acid, thiotaurine, and hypotaurine).

Also, not as the emulsifying agent but for the purpose of controlling tactile sensations during use, controlling drug permeation and such, or improving washability when blended into washing agents for skin and hair, surfactants can be blended into the water phase or oil phase of the oil-in-water emulsion composition of the present invention.

An ampholytic surfactant has at least one cationic functional group and one anionic functional group, is cationic when the solution is acidic and anionic when the solution is alkaline, and assumes characteristics similar to a nonionic surfactant around the isoelectric point.

Ampholytic surfactants are classified, based on the type of the anionic group, into the carboxylic acid type, the sulfuric ester type, the sulfonic acid type, and the phosphoric ester type. For the present invention, the carboxylic acid type, the sulfuric ester type, and the sulfonic acid type are preferable. The carboxylic acid type is further classified into the amino acid type and the betaine type. Particularly preferable is the betaine type.

Specific examples include: imidazoline type ampholytic surfactants (for example, 2-undecyl-N,N,N-(hydroxyethyl carboxymethyl)-2-imidazoline sodium salt and 2-cocoyl-2-imidazolinium hydroxide-1-carboxyethyloxy 2 sodium salt); and betaine type surfactants (for example, 2-heptadecyl-N-carboxymethyl-N-hydroxyethyl imidazolinium betaine, lauryldimethylaininoacetic acid betaine, alkyl betaine, amide betaine, and sulfobetaine).

Examples of cationic surfactants include quaternary ammonium salts such as cetyltrimethylammonium chloride, stearyltrimethylammonium chloride, behenyltrimehylammonium chloride, behenyldimethylhydroxyethylammonium chloride, stearyldimethylbenzylammonium chloride, and cetyltrimethylammonium methyl sulfate. Other examples include amide amine compounds such as stearic diethylaminoethylamide, stearic dimethylaminoethylamide, palmitic diethylaminoethylamide, palmitic dimethylaminoethylamide, myristic diethylaminoethylamide, myristic dimethylaminoethylamide, behenic diethylaminoethylamide, behenic dimethylaminoethylamide, stearic di ethyl am inopropylamide, stearic dimethylaminopropylamide, palmitic diethylaminopropylamide, palmitic dimethylaminopropylamide, myristic diethylaminopropylamide, myristic dimethylaminopropylamide, behenic diethylaminopropylamide, and behenic dimethylaminopropylamide.

Anionic surfactants are classified into the carboxylate type such as fatty acid soaps, N-acyl glutamates, and alkyl ether acetates, the sulfonic acid type such as α-olefin sulfonates, alkane sulfonates, and alkylbenzene sulfonates, the sulfuric ester type such as higher alcohol sulfuric ester salts, and phosphoric ester salts. Preferable are the carboxylate type, the sulfonic acid type, and the sulfuric ester salt type; particularly preferable is the sulfuric ester salt type.

Specific examples include fatty acid soaps (for example, sodium laurate and sodium palmitate); higher alkyl sulfuric acid ester salts (for example, sodium lauryl sulfate and potassium lauryl sulfate); alkyl ether sulfuric acid ester salts (for example, POE-triethanolamine lauryl sulfate and sodium POE-lauryl sulfate); N-acyl sarcosinic acids (for example, sodium lauroyl sarcosinate); higher fatty acid amide sulfonic acid salts (for example, sodium N-myristoyl N-methyl taurate, sodium cocoyl methyl taurate, and sodium laurylmethyl taurate); phosphoric ester salts (for example, sodium POE-oleyl ether phosphate and POE stearyl ether phosphoric acid); sulfosuccinates (for example sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (for example, sodium linear dodecyl benzene sulfonate, triethanolamine linear dodecyl benzene sulfonate, and linear dodecyl benzene sulfonic acid); higher fatty acid ester sulfates (for example, hydrogenated coconut oil aliphatic acid glycerin sodium sulfate); N-acyl glutamates (for example, mono sodium N-lauroylglutarnate, disodium N-stearoylglutamate, and sodium N-myristoyl-L-glutamate); sulfated oils (for example, turkey red oil); POE-alkyl ether carboxylic acid; POE-alkyl aryl ether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

A nonionic surfactant is a surfactant that is not ionized to assume an electric charge in an aqueous solution. For the hydrophobic group, a type that uses alkyls and a type that uses dimethyl silicone are known among others. Specific examples of the former include glycerol fatty acid esters, ethylene oxide derivatives of glycerol fatty acid esters, polyglycerol fatty acid esters, propylene glycol fatty acid esters, ethylene oxide derivatives of propylene glycol fatty acid esters, polyethylene glycol fatty acid esters, polyethylene glycol alkyl ethers, polyethylene glycol alkyl phenyl ethers, polyethylene glycol castor oil derivatives, and polyethylene glycol hydrogenated castor oil derivatives. Examples of the latter include polyether-modified silicone and polyglycerin-modified silicone. Preferable is the type that uses alkyl for the hydrophobic group.

Specific examples of lipophilic nonionic surfactants include sorbitan fatty acid esters (for example, sorbitan mono oleate, sorbitan mono isostearate, sorbitan mono laurate, sorbitan mono palmitate, sorbitan mono stearate, sorbitan sesquioleate, sorbitan trioleate, diglycerol sorbitan penta-2-ethylhexylate, diglycerol sorbitan tetra-2-ethylhexylate); glycerin polyglycerin aliphatic acids (for example, mono cottonseed oil fatty acid glycerin, glyceryl monoerucate, glycerin sesquioleate, glyceryl monostearate, α, α'-glycerin oleate pyroglutamate, monostearate glycerin malic acid); propylene glycol fatty acid esters (for example, propylene glycol monostearate); hydrogenated castor oil derivatives; and glycerin alkylethers.

Examples of hydrophilic nonionic surfactants include POE-sorbitan fatty acid esters (for example, POE-sorbitan monooleate, POE-sorbitan monostearate, POE-sorbitan monooleate, and POE-sorbitan tetraoleate); POE sorbitol fatty acid esters (for example, POE sorbitol monolaurate, POE-sorbitol monooleate, POE-sorbitolpentaoleate, and POE-sorbitol monostearate); POE-glycerin fatty acid esters (for example, POE-monooleates such as POE-glycerin monostearate, POE-glycerin monoisostearate, and POE-glycerin triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE-2-octyl dodecyl ether, and POE-cholestanol ether); pluaronics (for example, pluaronic); POE.cndot. POP-alkylethers (for example, POE.cndot. POP-cetyl ether, POE.cndot. POP-2-decyl tetradecyl ether, POE.cndot. POP-monobutyl ether, POE.cndot. POP-lanolin hydrate, and POE.cndot. POP-glycerin ether); tetra POE.cndot, tetra POP-ethylenediamino condensates (for example, tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax-lanolin derivatives (for example, POE-sorbitol beeswax); alkanol amides (for example, palm oil fatty acid diethanol amide, laurate monoethanolamide, and fatty acid isopropanol amide); POE-propylene glycol fatty acid esters; POE-alkylamines; POE-fatty acid amides; sucrose fatty acid esters; alkyl ethoxydimethylamine oxides; and trioleyl phosphoric acid.

Applications of oil-in-water emulsion cosmetic and white cloudy cosmetic of the present invention are not limited; since it suppresses skin irritation and manifests superior feeling in use, it can be commercialized as skin cosmetics, hair cosmetics, skin external preparations, and etc.

Examples

The present invention will be further described in the following examples. However, the invention is not limited by these examples. First, production examples of the raw material for cosmetics (core-corona type microgel dispersion liquid) used in Examples are shown. Unless otherwise specified, the blending quantity of each component will be expressed in % by mass.

<Production Method of Raw Material for Cosmetics (Core-Corona Type Microgel Dispersion)>

Polyethyleneoxide macro monomer, hydrophobic monomer, and cross-linking monomer were added into 200 g of water-polyol mixed solvent in a three-neck flask equipped with a reflux tube and a nitrogen feeding tube. After sufficient dissolution or dispersion, 1 mol % of the polymerization initiator, 2,2'-azobis(2-methylpropionamidine) dihydrochloride, with respect to the total amount of monomers, was dissolved in a small amount of water and added, and further dissolution or dispersion was carried out. The uniformly dissolved or dispersed polymerization solution was put through nitrogen substitution for 20 minutes to remove dissolved oxygen, followed by 8 hours of polymerization with stirring by means of a magnetic stirrer while the temperature was maintained at 65 to 70° C. in an oil bath. After the completion of polymerization, the polymer solution was returned to room temperature; thus a core-corona type microgel dispersion was obtained.

As polyethyleneoxide macromonomer, BLEMMER PME-400, BLEMMER PME-1000, and BLEMMER PME-4000 (manufactured by NOF Corporation, macromonomer represented by chemical formula (1) ($n \approx 9$, $n \approx 23$, and $n \approx 90$, respectively)) were used. As hydrophobic monomer, methyl methacrylate (MMA), butyl methacrylate (n-BMA), 2-ethylhexyl methacrylate (EHMA) were used. As cross-linking monomer, ethylene glycol dimethacrylate (EGDMA) was used.

<Method for Measuring the Particle Size and the Degree of Dispersion>

The particle size of the core-corona type microgel (hereinafter sometimes abbreviated as "microgel") was measured using a Zetasizer from Malvern Instruments Ltd. Measurement samples of the microgel dispersion liquid with the microgel concentration of about 0.1% were prepared by dilution with water. After removing dust with a 0.45 μm filter, the scattering intensity at 25° C. was measured at the scattering angle of 173° (back-scattered light), the average particle size and the degree of dispersion were calculated with analysis software installed on the measurement apparatus. The particle size was analyzed by the cumulant analysis method. The degree of dispersion is a normalized value of the second-order cumulant value obtained by the cumulant analysis. The degree of dispersion is a commonly used parameter, and the automatic analysis is possible by using a commercial dynamic light scattering measurement apparatus. For the viscosity of the solvent, which was necessary for the particle size analysis, the viscosity of pure water at 25° C., i.e., 0.89 mPas, was used.

(Polyols Used as the Polymerization Solvent)

Under the polymerization conditions described in Table 1 and Table 2 below, the raw materials for cosmetics were produced by the above-described production method. For the respective samples, the determination of appearance and the measurement of the particle size and the degree of dispersion were carried out. The results are shown in Table 3.

In the tables below, polyols are represented by the following abbreviations. EtOH: ethanol, DPG: dipropylene glycol, BG: 1,3-butylene glycol, IPG: isoprene glycol, DG: glycerin.

TABLE 1

| | Macromonomer | Hydrophobic monomer | | Cross-linking monomer | Polymerization solvent | | |
|---|---|---|---|---|---|---|---|
| | PME-4000 Chemical formula (1) | MMA Chemical formula (2) | n-BMA | EGDMA Chemical formula (3) | Water | Polyols | Amounts of polyols |
| Production example 1 | 8.11 | 4.89 | 6.95 | 0.059 | 120 | EtOH | 80 |
| Production example 2 | 8.11 | 4.89 | 6.95 | 0.059 | 120 | DPG | 80 |
| Production example 3 | 8.11 | 4.89 | 6.95 | 0.059 | 120 | BG | 80 |
| Production example 4 | 8.11 | 4.89 | 6.95 | 0.059 | 120 | IPG | 80 |
| Production example 5 | 8.11 | 4.89 | 6.95 | 0.059 | 120 | DG | 80 |

※All units of values in Table 1 are gram.

TABLE 2

| | (A) Macromonomer/ hydrophobic monomer (mole/mole) | (B) Feed amount of cross-linking monomer (% by mass) | (C) Carbon atoms of hydrophobic monomer | (D) Polyols | (E) Water/polyol (mixed solvent ratio) |
|---|---|---|---|---|---|
| Production example 1 | 1/50 | 0.5 | 1, 4 | EtOH | 60/40 |
| Production example 2 | 1/50 | 0.5 | 1, 4 | DPG | 60/40 |
| Production example 3 | 1/50 | 0.5 | 1, 4 | BG | 60/40 |
| Production example 4 | 1/50 | 0.5 | 1, 4 | IPG | 60/40 |
| Production example 5 | 1/50 | 0.5 | 1, 4 | DG | 60/40 |

TABLE 3

| | Appearance | Particle size (nm) | Degree of dispersion |
|---|---|---|---|
| Production example 1 | white cloudy solution | 206.1 | 0.052 |
| Production example 2 | white cloudy solution | 211.8 | 0.019 |
| Production example 3 | white cloudy solution | 212.1 | 0.035 |
| Production example 4 | white cloudy solution | 205.2 | 0.029 |
| Production example 5 | generation of gigantic masses | — | — |

In Production Examples 1 to 4, wherein water-ethanol, water-dipropylene glycol, water-1,3-butylene glycol, or water-isoprene glycol was used as the polymerization solvent, a white cloudy dispersion was obtained after polymerization, and the evaluation of the particle size and the degree of dispersion was possible, so that the formation of microgel could be confirmed. On the other hand, in Production Example 5, wherein water-glycerin was used as the polymerization solvent, gigantic masses were formed after polymerization and fine microgel particles could not be formed. It is considered that the polymerization of microgel did not proceed because glycerin has low affinity to the hydrophobic monomer compared with ethanol, dipropylene glycol, 1,3-butylene glycol, or isoprene glycol.

(Water-Polyol Composition Ratio)

Under the polymerization conditions described in Table 4 and Table 5 below, the raw materials for cosmetics were produced by the above-described production method. For the respective samples, the determination of appearance and the measurement of the particle size and the degree of dispersion were carried out. The results are shown in Table 6.

TABLE 4

| | Macromonomer | Hydrophobic monomer | | Cross-linking monomer | Polymerization solvent | | |
|---|---|---|---|---|---|---|---|
| | PME-4000 Chemical formula (1) | MMA Chemical formula (2) | n-BMA | EGDMA Chemical formula (3) | Water | Polyols | Amounts of polyols |
| Production example 6 | 8.11 | 4.89 | 6.95 | 0.059 | 40 | DPG | 160 |
| Production example 7 | 8.11 | 4.89 | 6.95 | 0.059 | 80 | DPG | 120 |

TABLE 4-continued

|  | Macromonomer | Hydrophobic monomer | | Cross-linking monomer | Polymerization solvent | | |
|---|---|---|---|---|---|---|---|
|  | PME-4000 Chemical formula (1) | MMA Chemical formula (2) | n-BMA | EGDMA Chemical formula (3) | Water | Polyols | Amounts of polyols |
| Production example 8 | 8.11 | 4.89 | 6.95 | 0.059 | 120 | DPG | 80 |
| Production example 9 | 8.11 | 4.89 | 6.95 | 0.059 | 160 | DPG | 40 |
| Production example 10 | 8.11 | 4.89 | 6.95 | 0.059 | 180 | DPG | 20 |
| Production example 11 | 8.11 | 4.89 | 6.95 | 0.059 | 40 | BG | 160 |
| Production example 12 | 8.11 | 4.89 | 6.95 | 0.059 | 180 | BG | 20 |
| Production example 13 | 8.11 | 4.89 | 6.95 | 0.059 | 40 | IPG | 160 |
| Production example 14 | 8.11 | 4.89 | 6.95 | 0.059 | 180 | IPG | 20 |
| Production example 15 | 8.11 | 4.89 | 6.95 | 0.059 | 40 | EtOH | 160 |
| Production example 16 | 8.11 | 4.89 | 6.95 | 0.059 | 180 | EtOH | 20 |

※All units of values in Table 4 are gram.

TABLE 5

|  | (A) Macromonomer/ hydrophobic monomer (mole/mole) | (B) Feed amount of cross-linking monomer (% by mass) | (C) Carbon atoms of hydrophobic monomer | (D) Polyols | (E) Water/polyol (mixed solvent ratio) |
|---|---|---|---|---|---|
| Production example 6 | 1/50 | 0.5 | 1, 4 | DPG | 20/80 |
| Production example 7 | 1/50 | 0.5 | 1, 4 | DPG | 40/60 |
| Production example 8 | 1/50 | 0.5 | 1, 4 | DPG | 60/40 |
| Production example 9 | 1/50 | 0.5 | 1, 4 | DPG | 80/20 |
| Production example 10 | 1/50 | 0.5 | 1, 4 | DPG | Oct-90 |
| Production example 11 | 1/50 | 0.5 | 1, 4 | BG | 20/80 |
| Production example 12 | 1/50 | 0.5 | 1, 4 | BG | Oct-90 |
| Production example 13 | 1/50 | 0.5 | 1, 4 | IPG | 20/80 |
| Production example 14 | 1/50 | 0.5 | 1, 4 | IPG | Oct-90 |
| Production example 15 | 1/50 | 0.5 | 1, 4 | EtOH | 20/80 |
| Production example 16 | 1/50 | 0.5 | 1, 4 | EtOH | Oct-90 |

TABLE 6

|  | Appearance | Particle size (nm) | Degree of dispersion |
|---|---|---|---|
| Production example 6 | white cloudy solution | 244.6 | 0.052 |
| Production example 7 | white cloudy solution | 216.2 | 0.041 |
| Production example 8 | white cloudy solution | 211.8 | 0.019 |
| Production example 9 | white cloudy solution | 153.6 | 0.083 |
| Production example 10 | white cloudy solution | 200.8 | 0.284 |
| Production example 11 | white cloudy solution | 248.2 | 0.02 |

TABLE 6-continued

|  | Appearance | Particle size (nm) | Degree of dispersion |
|---|---|---|---|
| Production example 12 | white cloudy solution | 145.1 | 0.08 |
| Production example 13 | white cloudy solution | 189 | 0.058 |
| Production example 14 | white cloudy solution | 153.1 | 0.069 |
| Production example 15 | translucent homogeneous solution | — | — |

(Ratio of Macromonomer/Hydrophobic Monomer, Amount of Cross-Linking Monomer, and Hydrophobic Monomer Species)

Under the polymerization conditions described in Table 4 and Table 5 below, the raw materials for cosmetics were produced by the above-described production method, 60 g of water and 140 g of dipropylene glycol are used as the polymerization solvent.

For the respective samples, the determination of appearance and the measurement of the particle size and the degree of dispersion were carried out. The results are shown in Table 6.

TABLE 7

|  | Macromonomer | | | Hydrophobic monomer | | | Cross-linking monomer EGDMA |
|---|---|---|---|---|---|---|---|
|  | PME-4000 | PME-1000 | PME-400 | MMA | n-BMA | EHMA | Chemical formula (3) |
|  | Chemical formula (1) | | | Chemical formula (2) | | | |
| Production example 17 | 3.7 | — | — | 6.7 | 9.52 | — | 0.081 |
| Production example 18 | 11.54 | — | — | 3.48 | 4.94 | — | 0.042 |
| Production example 19 | 8.12 | — | — | 4.9 | 6.95 | — | 0.036 |
| Production example 20 | 8.08 | — | — | 4.88 | 6.92 | — | 0.12 |
| Production example 21 | 9.04 | — | — | 10.91 | — | — | 0.055 |
| Production example 22 | 7.35 | — | — | — | 12.589 | — | 0.063 |
| Production example 23 | 5.88 | — | — | — | — | 14.05 | 0.07 |
| Production example 24 | — | 3.18 | — | 6.92 | 9.82 | — | 0.084 |
| Production example 25 | — | — | 1.66 | 7.54 | 10.71 | — | 0.091 |

※All units of values in Table 7 are gram.

TABLE 6-continued

|  | Appearance | Particle size (nm) | Degree of dispersion |
|---|---|---|---|
| Production example 16 | white cloudy solution | 214.3 | 0.105 |

In Production Examples 6 to 14, wherein water-dipropylene glycol, water-1,3-butylene glycol, or water-isoprene glycol was used as the polymerization solvent and the solvent composition was water/polyol=a range of 20/80 to 90/10, and in Production Example 16, wherein the polymerization solvent was water/ethanol=90/10, a white cloudy dispersion was obtained after polymerization. The evaluation of the particle size and the degree of dispersion was possible, so that the formation of microgel could be confirmed.

On the other hand, in Production Example 15, wherein water/ethanol=20/80 was used as the polymerization solvent, it was a translucent homogeneous solution state even after polymerization, and fine microgel particles could not be formed. It is considered that the emulsion polymerization did not proceed and fine microgel particles could not be formed in the polymerization solvent with the composition of high ethanol concentration because ethanol has a high solubility of the hydrophobic monomer and an emulsion in which the hydrophobic monomer is the nucleus could not be formed.

TABLE 8

|  | (A) Macromonomer/ hydrophobic monomer (mole/mole) | (B) Feed amount of cross-linking monomer (% by mass) | (C) Carbon atoms of hydrophobic monomer | (D) Polyols | (E) Water/ polyol (mixed solvent ratio) |
|---|---|---|---|---|---|
| Production example 17 | 1/150 | 0.5 | 1, 4 | DPG | 30/70 |
| Production example 18 | 1/25 | 0.5 | 1, 4 | DPG | 30/70 |
| Production example 19 | 1/50 | 0.3 | 1, 4 | DPG | 30/70 |
| Production example 20 | 1/50 | 1 | 1, 4 | DPG | 30/70 |
| Production example 21 | 1/50 | 0.5 | 1 | DPG | 30/70 |
| Production example 22 | 1/50 | 0.5 | 4 | DPG | 30/70 |
| Production example 23 | 1/50 | 0.5 | 8 | DPG | 30/70 |
| Production example 24 | 1/50 | 0.5 | 1, 4 | DPG | 30/70 |
| Production example 25 | 1/50 | 0.5 | 1, 4 | DPG | 30/70 |

TABLE 9

|  | Appearance | Particle size (nm) | Degree of dispersion |
|---|---|---|---|
| Production example 17 | white cloudy solution | 278.5 | 0.166 |
| Production example 18 | white cloudy solution | 194.5 | 0.052 |
| Production example 19 | white cloudy solution | 240 | 0.127 |
| Production example 20 | white cloudy solution | 331.6 | 0.136 |
| Production example 21 | white cloudy solution | 263.8 | 0.28 |
| Production example 22 | white cloudy solution | 286 | 0.224 |
| Production example 23 | white cloudy solution | 264.3 | 0.061 |
| Production example 24 | white cloudy solution | 319.3 | 0.15 |
| Production example 25 | white cloudy solution | 472 | 0.103 |

In Production Examples 17 to 25, wherein water/dipropylene glycol 30/70 was used as the polymerization solvent, and condition (A) the loading mole ratio of macromonomer/hydrophobic monomer, condition (B) the amount of loaded cross-linking monomer, condition (C) the number of carbon atoms of hydrophobic monomer, and conditions (D) and (E), which are polymerization solvent conditions, were all satisfied, a white cloudy dispersion was obtained after polymerization in all the cases, and the evaluation of the particle size and the degree of dispersion was possible; thus the formation of microgel could be confirmed.

In the following, examples of cosmetics in which the raw material for cosmetics of the above-described production examples was blended are shown.

Prior to illustrating the examples, the methods for the evaluation tests used in the present invention will be explained.

Evaluation (1): Transparency (White Turbidity)

Samples were measured with a Spectrophotometer V-630 (manufactured by JASCO Corporation) at a wavelength of 600 nm, and the evaluation was carried out based on the visible light transmittance (light path length: 1 cm). Ion-exchanged water was used as the reference.

Evaluation (2-1): Stability (Appearance)

On day after sample preparation, the appearance was visually observed.

A: The sample was homogeneous and no oil separation or aggregation was observed.

B: The sample was mostly homogeneous but slight oil separation was observed.

C: The sample was not homogeneous or significant oil separation or powder aggregation was observed.

Evaluation (2-2): Emulsion Stability (Emulsion Particles)

Emulsified particles of the sample were observed with an optical microscope.

A: The sample was homogeneous and no coalescence or aggregation was observed.

B: The sample was mostly homogeneous but slight coalescence and/or aggregation was observed.

C: The sample was not homogeneous, or significant coalescence or powder aggregation was observed.

Evaluation (3): Skin Irritation Test

An occlusive patch was applied to the inner upper arm of 10 sensitive skin panelists for 24 hours and the skin was evaluated based on the following criteria.

0 . . . Absolutely no abnormality was observed.
1 . . . Slight reddening was observed.
2 . . . Reddening was observed.
3 . . . Reddening and a papule were observed.

The evaluation criteria of the "skin irritation test" are as follows:

A: The average score given by 10 panelists is 0 or higher but less than 0.15.

B: The average score given by 10 panelists is 0.15 or higher but less than 0.2.

C: The average score given by 10 panelists is 0.2 or higher but less than 0.3.

D: The average score given by 10 panelists is 0.3 or higher.

Evaluation (4): Feeling in Use

The feeling in use ("non-stickiness", "rich feeling", and "fast skin compatibility"), when the sample was applied on the skin, was evaluated by 10 professional panelists based on the following criteria.

A: 7 or more of 10 panelists answered "good" or "really agreeable".

B: 5 or more of 10 panelists answered "good" or "really agreeable".

C: 3 or more of 10 panelists answered "good" or "really agreeable".

D: 2 or less of 10 panelists answered "good" or "really agreeable".

Evaluation (5): Stability Over Time

The oil-in-water emulsion composition was observed with the naked eye one month after preparation.

A: The sample was maintained as-is the emulsified state when prepared.

B: Some sedimentation/floatation were observed; however, the sample was nearly maintained as the emulsion state.

C: Sedimentation/floatation of emulsion particles were observed and coalescence of the particles was also observed.

D: Sedimentation/floatation/coalescence of emulsion were observed and the oil phase was completely separated.

Evaluation (6): Durability of Fragrance

The durability of fragrance was evaluated by 10 professional panelists based on the following criteria.

A: 7 or more of 10 panelists answered "good" or "really durable".

B: 5 or more of 10 panelists answered "good" or "really durable".

C: 3 or more of 10 panelists answered "good" or "really durable".

D: 2 or less of 10 panelists answered "good" or "really durable".

Example 1: White Cloudy Cosmetic

The present inventors produced white cloudy cosmetics (lotion), wherein the above-described raw material for cosmetics was blended with the blending compositions listed in Table 10 below, by the common production method. For the respective samples, the evaluation was carried out by the above-described evaluation methods (1), (2-1), (3), and (4). The results are shown in Table 10.

In all the cases, the polymerization solvent remained in the raw material for cosmetics (core-corona type microgel dispersion). The polymerization solvent, water and ethanol or polyol, is also contained in the white cloudy cosmetic; therefore, their concentrations are shown in the table.

TABLE 10

| | Test Examples (%) | | | | | | | |
|---|---|---|---|---|---|---|---|---|
| | 1-1 | 1-2 | 1-3 | 1-4 | 1-5 | 1-6 | 1-7 | 1-8 |
| Ion-exchanged water | balance | balance | balance | balance | balance | balance | balance | balance |
| Glycerin | 5 | 5 | 5 | 5 | 5 | 5 | 5 | 5 |
| Polyethyleneglycol 1000 | 1 | 1 | 1 | 1 | 1 | 1 | 1 | 1 |
| *Paeonia suffruticosa* root extract solution | 0.01 | 0.01 | 0.01 | 0.01 | 0.01 | 0.01 | 0.01 | 0.01 |
| *Rubus idaeus* fruit extract solution | 0.01 | 0.01 | 0.01 | 0.01 | 0.01 | 0.01 | 0.01 | 0.01 |
| *Saxifraga sarmentosa* extract solution | 0.01 | 0.01 | 0.01 | 0.01 | 0.01 | 0.01 | 0.01 | 0.01 |
| Menthol | 0.02 | 0.02 | 0.02 | 0.02 | 0.02 | 0.02 | 0.02 | 0.02 |
| Citric acid (food) | 0.02 | 0.02 | 0.02 | 0.02 | 0.02 | 0.02 | 0.02 | 0.02 |
| Sodium citrate | 0.08 | 0.08 | 0.08 | 0.08 | 0.08 | 0.08 | 0.08 | 0.08 |
| Sodium hexametha phosphate | 0.03 | 0.03 | 0.03 | 0.03 | 0.03 | 0.03 | 0.03 | 0.03 |
| Phenoxyethanol | 0.3 | 0.3 | 0.3 | 0.3 | 0.3 | 0.3 | 0.3 | 0.3 |
| Perfume | 0.05 | 0.05 | 0.05 | 0.05 | 0.05 | 0.05 | 0.05 | 0.05 |
| Microgel dispersion liquid of production example 1 | 1 | — | — | — | — | — | — | — |
| Microgel dispersion liquid of production example 2 | — | 1 | — | — | — | — | — | — |
| Microgel dispersion liquid of production example 3 | — | — | 1 | — | — | — | — | — |
| Microgel dispersion liquid of production example 4 | — | — | — | 1 | — | — | — | — |
| Microgel dispersion liquid of production example 10 | — | — | — | — | 1 | — | — | — |
| Microgel dispersion liquid of production example 12 | — | — | — | — | — | 1 | — | — |
| Microgel dispersion liquid of production example 14 | — | — | — | — | — | — | 1 | — |
| Microgel dispersion liquid of production example 16 | — | — | — | — | — | — | — | 1 |
| The concentration of core-corona type microgel in the microgel dispersion liquid | 0.1 | 0.1 | 0.1 | 0.1 | 0.1 | 0.1 | 0.1 | 0.1 |
| The concentration of water in the microgel dispersion liquid | 0.54 | 0.54 | 0.54 | 0.54 | 0.81 | 0.81 | 0.81 | 0.81 |
| The concentration of ethanol in the microgel dispersion liquid | 0.36 | — | — | — | — | — | — | 0.09 |
| The concentration of dipropylene glycol in the microgel dispersion liquid | — | 0.36 | — | — | 0.09 | — | — | — |
| The concentration of 1,3-buthylene glycol in the microgel dispersion liquid | — | — | 0.36 | — | — | 0.09 | — | — |
| The concentration of isoprene glycol in the microgel dispersion liquid | — | — | — | 0.36 | — | — | 0.09 | — |
| Evaluation (1): 600 nm transparency (%) | 36.7 | 48.2 | 45.7 | 50.3 | 35.5 | 84 | 83.3 | 56.2 |
| Evaluation (2-1): Stability | A | A | A | A | A | A | A | A |
| Evaluation (3): Skin Irritation | C | A | A | B | A | A | B | C |
| Evaluation (4-1): Non-stickiness | A | A | A | A | A | A | A | A |
| Evaluation (4-2): Rich feeling | B | A | A | A | B | B | B | B |
| Evaluation (4-3): Fast skin compatibility | B | A | A | A | B | B | B | B |

As shown in Table 10, all of the white cloudy cosmetics of Test Examples 1-1 to 1-8, wherein the microgel dispersion liquid of Production Examples 1 to 4, 10, 12, 14, or 16 was blended, displayed a turbid appearance of white turbidity to pale translucence and were excellent in stability and the feeling in use. However, white cloudy lotions of Test Examples 1-1 and 1-8, wherein the microgel dispersion liquid of Production Example 1 or Production Example 16 containing ethanol was blended, generated some skin irritation to the panelists with sensitive skin.

Thus, the white cloudy cosmetics without ethanol, wherein a core-corona type microgel dispersion, produced by using a polyol as the polymerization solvent instead of ethanol, was blended, displayed not only good stability and the feeling in use but also low irritation.

Example 2: Oil-in-Water Emulsion Cosmetic

Subsequently, the present inventors produced oil-in-water emulsion cosmetics, wherein the above-described raw material for cosmetics was blended with the blending compositions listed in Table 11 below, by the below-described production method. For the respective samples, the evaluation was carried out by the above-described evaluation methods (2) to (5). The results are shown in Table 11.

In all the cases, the polymerization solvent remained in the raw material for cosmetics (core-corona type microgel dispersion). The polymerization solvent, water and ethanol or polyol, is also contained in the oil-in-water emulsion cosmetic; therefore, their concentrations are shown in the table.

Method for Producing the Oil-in-Water Emulsion Cosmetic

Various water phase components such as polyols and thickeners were added to purified water and mixed. Added the raw material for cosmetics of the present invention to the mixture, and stirring and mixing. The raw material for cosmetics and the water phase components were homogeneously dispersed, to which the oil phase components were added, followed by shear mixing with a homomixer until homogeneous to obtain the oil-in-water emulsified composition.

TABLE 11

| | Test Examples (%) | | | | | | | |
|---|---|---|---|---|---|---|---|---|
| | 2-1 | 2-2 | 2-3 | 2-4 | 2-5 | 2-6 | 2-7 | 2-8 |
| Ion-exchanged water | balance | balance | balance | balance | balance | balance | balance | balance |
| Liquid paraffin | 10 | 10 | 10 | 10 | 10 | 10 | 10 | 10 |
| Glyceryl tri-2-ethylhexanoate | 10 | 10 | 10 | 10 | 10 | 10 | 10 | 10 |
| Dimethylpolysiloxane (6cs) | 10 | 10 | 10 | 10 | 10 | 10 | 10 | 10 |
| Carboxyvinylpolymer | 0.1 | 0.1 | 0.1 | 0.1 | 0.1 | 0.1 | 0.1 | 0.1 |
| Potassium hydroxide | 0.06 | 0.06 | 0.06 | 0.06 | 0.06 | 0.06 | 0.06 | 0.06 |
| Phenoxyethanol | 0.3 | 0.3 | 0.3 | 0.3 | 0.3 | 0.3 | 0.3 | 0.3 |
| Chelator | proper quantity | proper quantity | proper quantity | proper quantity | proper quantity | proper quantity | proper quantity | proper quantity |
| Perfume | proper quantity | proper quantity | proper quantity | proper quantity | proper quantity | proper quantity | proper quantity | proper quantity |
| Microgel dispersion liquid of production example 1 | 10 | — | — | — | — | — | — | — |
| Microgel dispersion liquid of production example 2 | — | 10 | — | — | — | — | — | — |
| Microgel dispersion liquid of production example 3 | — | — | 10 | — | — | — | — | — |
| Microgel dispersion liquid of production example 4 | — | — | — | 10 | — | — | — | — |
| Microgel dispersion liquid of production example 6 | — | — | — | — | 10 | — | — | — |
| Microgel dispersion liquid of production example 8 | — | — | — | — | — | 10 | — | — |
| Microgel dispersion liquid of production example 9 | — | — | — | — | — | — | 10 | — |
| Microgel dispersion liquid of production example 10 | — | — | — | — | — | — | — | 10 |
| The concentration of core-corona type microgel in the microgel dispersion liquid | 1 | 1 | 1 | 1 | 1 | 1 | 1 | 1 |
| The concentration of water in the microgel dispersion liquid | 5.4 | 5.4 | 5.4 | 5.4 | 1.8 | 3.6 | 7.2 | 8.1 |
| The concentration of ethanol in the microgel dispersion liquid | 3.6 | — | — | — | — | — | — | — |
| The concentration of dipropylene glycol in the microgel dispersion liquid | — | 3.6 | — | — | 7.2 | 5.4 | 1.8 | 0.9 |
| The concentration of 1,3-buthylene glycol in the microgel dispersion liquid | — | — | 3.6 | — | — | — | — | — |
| The concentration of isoprene glycol in the microgel dispersion liquid | — | — | — | 3.6 | — | — | — | — |
| Evaluation (2-1): Emulsion stability (appearance) | A | A | A | A | A | A | A | A |
| Evaluation (2:2): Emulsion stability (Particles) | A | A | A | A | A | A | A | A |
| Evaluation (3): Skin Irritation | D | A | A | B | B | A | A | A |
| Evaluation (4-1): Dewy Freshness | A | A | A | A | A | A | A | A |
| Evaluation (4-2): Non-frictional feelings | A | A | A | A | A | A | A | A |
| Evaluation (4-3): Non-powdery sensation | A | A | A | A | A | A | A | A |
| Evaluation (5): Stability over time | A | A | A | A | A | A | C | C |

As shown in Table 11, all of the oil-in-water emulsion cosmetics of Test Examples 2-1 to 2-8, wherein the microgel dispersion liquid of Production Examples 1 to 4, 6, or 8 to 10 was blended as the emulsifier, were excellent in emulsion stability, feeling in use, and stability over time. However, the oil-in-water emulsion cosmetic of Test Example 2-1, wherein the microgel dispersion liquid of Production Example 1 containing ethanol was blended, generated skin irritation to the panelists with sensitive skin.

Thus, the oil-in-water emulsion cosmetics without ethanol, wherein a core-corona type microgel dispersion, produced by using a polyol as the polymerization solvent instead of ethanol, was blended, displayed not only good stability and the feeling in use but also low irritation.

Subsequently, the present inventors produced oil-in-water emulsion cosmetics, wherein the above-described raw material for cosmetics (production example 11) was blended with the blending compositions listed in Table 12 below, by the below-described production method. For the respective samples, the evaluation was carried out by the above-described evaluation methods (2) to (5). The results are shown in Table 12.

TABLE 12

|  | Test Examples (%) | | | | | |
| --- | --- | --- | --- | --- | --- | --- |
|  | 3-1 | 3-2 | 3-3 | 3-4 | 3-5 | 3-6 |
| Ion-exchanged water | balance | balance | balance | balance | balance | balance |
| Isododecane | 3 | 5 | 10 | 20 | 30 | 40 |
| Cetyl octanoate | 3 | 5 | 10 | 20 | 30 | 40 |
| Carboxyvinylpolymer | 0.2 | 0.2 | 0.15 | 0.1 | 0.05 | — |
| Potassium hydroxide | 0.12 | 0.12 | 0.09 | 0.06 | 0.03 | — |
| Phenoxyethariol | 0.3 | 0.3 | 0.3 | 0.3 | 0.3 | 0.3 |
| Chelator | proper quantity | proper quantity | proper quantity | proper quantity | proper quantity | proper quantity |
| Microgel dispersion liquid of production example 11 | 10 | 10 | 10 | 10 | 10 | 10 |
| Evaluation (2-1): Emulsion stability (appearance) | A | A | A | A | A | A |
| Evaluation (2-2): Emulsion stability (Particles) | A | A | A | A | A | A |
| Evaluation (3): Skin Irritation | A | A | A | A | A | A |
| Evaluation (4-1): Dewy freshness | A | A | A | A | B | B |
| Evaluation (4-2): Non-frictional feelings | B | B | A | A | A | A |
| Evaluation (4-3): Non-powdery sensation | A | A | A | A | A | A |
| Evaluation (5): Stability over time | A | A | A | A | A | A |

※The concentration of core-corona type microgel in the core-corona dispersion liquid: 1%

The concentration of water in the core-corona dispersion liquid: 1.8%

The concentration of 1,3-butylene glycol in the core-corona dispersion liquid: 7.2%

As shown in Table 12, all of the oil-in-water emulsion cosmetics of Test Examples 3-1 to 3-6, wherein the microgel dispersion liquid of Production Example 11 was blended as the emulsifier, were excellent in emulsion stability, feeling in use, and stability over time, and the irritation was low.

Thus, the oil-in-water emulsion cosmetics, wherein a core-corona type microgel dispersion, produced by using the polyol, 1,3-butylene glycol, as the polymerization solvent instead of ethanol, was blended, displayed not only good stability and the feeling in use but also low irritation.

Subsequently, the present inventors produced oil-in-water emulsion fragrance cosmetics (Test example 4-1 to 4-3), wherein the raw material for cosmetics of the present invention (production example 19) was blended, by the above-described production method. Moreover, the present inventors produced conventional fragrance cosmetics (Test example 4-4 to 4-6) by the common production method. For the respective samples, the evaluation was carried out by the above-described evaluation methods (2) to (6). The results are shown in Table 13.

TABLE 13

|  | Test Examples (%) | | | | | |
| --- | --- | --- | --- | --- | --- | --- |
|  | 4-1 | 4-2 | 4-3 | 4-4 | 4-5 | 4-6 |
| Ion-exchanged water | balance | balance | balance | — | — | — |
| Ethanol | — | — | — | balance | balance | balance |

TABLE 13-continued

|  | Test Examples (%) | | | | | |
| --- | --- | --- | --- | --- | --- | --- |
|  | 4-1 | 4-2 | 4-3 | 4-4 | 4-5 | 4-6 |
| Dimethylacrylamide/sodium acryloyldimethyltaurate crosspolymer | 1 | 1 | 1 | 1 | 1 | 1 |
| Floral-aroma perfume in Table 14 | 5 | 8 | 20 | 5 | 8 | 20 |
| Phenoxyethanol | 0.3 | 0.3 | 0.3 | — | — | — |
| Chelator | proper quantity | proper quantity | proper quantity | proper quantity | proper quantity | proper quantity |
| Microgel dispersion liquid of production example 19 | 15 | 15 | 15 | — | — | — |
| Evaluation (2-1): Emulsion stability (appearance) | A | A | A | — | — | — |
| Evaluation (2-2): Emulsion stability (Particles) | A | A | A | — | — | — |
| Evaluation (3): Skin Irritation | A | A | B | D | D | D |
| Evaluation (4-1): Dewy freshness | A | A | A | C | C | C |
| Evaluation (4-2): Non-frictional feelings | A | A | A | D | C | C |
| Evaluation (4-3): Non-powdery sensation | A | A | A | A | A | A |
| Evaluation (5): Stability over time | A | A | A | A | A | A |
| Evaluation (6): Durability of fragrance | B | B | A | D | D | C |

※The concentration of core-corona type microgel in the core-corona type microgel dispersion liquid: 1.5%

The concentration of water in the core-corona type microgel dispersion liquid: 4.05%

The concentration of 1,3-butylene glycol in the core-corona type microgel dispersion liquid: 9.45%

The formulation of a floral-aroma perfume is shown below.

TABLE 14

|  | (%) |
| --- | --- |
| Orange oil | 4 |
| Lemon oil | 3 |
| Dihydromyrcenol | 3 |
| Linalool | 15 |
| Rose base | 12 |
| Terpineol | 5 |
| β-methyl ionone | 5 |
| β-ionone | 5 |
| Vertofix | 10 |
| Hedione | 18 |
| Florosa (FLOROSA, manufactured by Quest Int.) | 20 |

As shown in Table 13, all of the perfume-blended oil-in-water emulsion cosmetics of Test Examples 4-1 to 4-3, wherein the microgel dispersion liquid of Production Example 19 was blended as the emulsifier, were excellent in emulsion stability, feeling in use, and stability over time. Samples of Test Examples 4-1 to 4-3 were low in skin irritation and excellent in fragrance persistence compared with the samples of the conventional fragrance base type, wherein perfume is dissolved in ethanol (Test Examples 4-4 to 4-6).

In the following are listed the formulation examples of various cosmetics, wherein the presently invented raw material for cosmetics, polymerized in the water-polyol solvent system, was blended; however, the present invention is not limited by these examples. All of the cosmetics obtained from the following formulation examples manifested a high stability, low skin irritation, and superior feeling in use.

Example 1: Whitening Lotion

| | |
| --- | --- |
| Microgel dispersion liquid of production example 18 (Microgel in the dispersion liquid: 0.3%, water: 0.81%, dipropylene glycol: 1.89%) | 3 |
| Dipropylene glycol | 1 |
| Polyethylene glycol 1000 | 1 |
| Polyoxyethylene methyl glycoside | 1 |
| Glyceryl tri-2-ethylhexanoate | 0.1 |
| Polyoxyethylene hydrogenated castor oil | 0.2 |
| Polyglyceryl diisostearate | 0.15 |
| Sodium N-stearoyl-L-glutamate | 0.1 |
| Citric acid | 0.05 |
| Sodium citrate | 0.2 |
| Potassium hydroxide | 0.4 |
| Dipotassium glycyrrhizinate | 0.1 |
| Arginine hydrochloride | 0.1 |
| Dead nettle extract | 0.1 |
| Tranexamic acid | 2 |
| Potassium 4-methoxysalicylate | 1 |
| Trisodium edetate | 0.05 |
| 2-ethylhexyl paramethoxy cinnamate | 0.01 |
| Dibutyl hydroxytoluene | proper quantity |
| Paraben | proper quantity |
| Deep ocean water | 3 |
| Purified water | balance |
| Perfume | proper quantity |

Example 2: Thick Lotion

| | |
| --- | --- |
| Microgel dispersion liquid of production example 19 (Microgel in the dispersion liquid: 0.1%, water: 0.27%, dipropylene glycol: 0.63%) | 1 |
| Glycerin | 0.5 |
| Dipropylene glycol | 2.0 |
| 1,3-buthylene glycol | 6 |
| Rosemarry oil | 0.01 |
| Sage oil | 0.01 |
| Citric acid | 0.02 |
| Sodium citrate | 0.08 |
| Sodium hexametha phosphate | 0.03 |
| Hydroxypropyl-β-cyclodexirtrin | 0.1 |
| *Sapindus mukorossi* peel extract | 0.1 |

Example 3: Beauty Essence

| | |
|---|---|
| Microgel dispersion liquid of production example 20 (Microgel in the dispersion liquid: 0.1%, water: 0.27%, dipropylene glycol; 0.63%) | 1.0 |
| Glycerin | 1.0 |
| 1,3-buthylene glycol | 5.0 |
| Octyl methoxy cinnmamate | 0.2 |
| Liquid paraffin | 0.02 |
| Sodium hexametha phosphate | 0.03 |
| Trimethyl glycine | 1.0 |
| Sodium polyaspartate | 0.1 |
| 2-L-ascorbic acid α-tocopherol phosphoric acid diester potassium salt | 0.1 |
| Thiotaurine | 0.1 |
| *Camellia sinensis* extract | 0.1 |
| *Mentha piperita* leaf extract | 0.1 |
| *Iris florentina* root extract | 0.1 |
| Trisodium ethylenediaminetetraacetate | 0.1 |
| Carboxyvinylpolymer | 0.05 |
| Potassium hydroxide | 0.02 |
| Phenoxy ethanol | proper quantity |
| Purified water | balance |
| Perfume | proper quantity |

*Rosa multiflora* fruit extract 0.1
*Lilium candidum* bulb Extract 0.1
*Phellodendron amurense* bark extract 0.1
*Rosa roxburghii* fruit extract 0.1
*Rubus idaeus* fruit extract 0.1
Lavender oil 0.1
Peach kernel extract 0.1
Retinol 0.02
Sodium alginate 0.001
Purified water balance

Example 4: Milky Lotion

| | |
|---|---|
| Microgel dispersion liquid of production example 21 (Microgel in the dispersion liquid: 0.5%, water: 1.35%, dipropylene glycol: 3.15%) | 5 |
| Dimethylpolysiloxane 6cs | 3 |
| Glycerin | 6 |
| 1,3-buthylene glycol | 5 |
| Octyl methoxy cinnamate | 3 |
| Sunflower oil | 1 |
| Squalane | 2 |
| Potassium hydroxide | 0.1 |
| Sodium hexametha phosphate | 0.05 |
| Hydroxypropyl-β-cyclodexirtrin | 0.1 |
| Dipotassium glycyrrhizinate | 0.05 |
| *Eriobotrya japonica* leaf extract | 0.1 |
| Sodium L-glutamate | 0.05 |
| *Foeniculum vulgare* fruit extract | 0.1 |
| Yeast extract | 0.1 |
| Lavender oil | 0.1 |
| *Rehmannia chinensis* extract | 0.1 |
| Dimorpholino pyridazinone | 0.1 |
| Xanthane gum | 0.1 |
| Carboxyvinylpolymer | 0.1 |
| Colcothar | proper quantity |
| Yellow iron oxide | proper quantity |
| Paraben | proper quantity |
| Purified water | balance |

Example 5: Moisturizing Cream

| | |
|---|---|
| Microgel dispersion liquid of production example 22 (Microgel in the dispersion liquid: 0.8%, water: 2.16%, dipropylene glycol: 5.04%) | 8 |
| Liquid paraffin | 10 |
| Dimethylpolysiloxane 6cs | 5 |
| Squalane | 15 |
| Pentaerythritol tetra-2-ethylhexanoate | 5 |
| Glyceryl tri-2-ethylhexanoate | 10 |
| Glycerin | 10 |
| 1,3-buthylene glycol | 2 |
| Erythritol | 1 |
| Polyethylene glycol 1500 | 5 |
| Potassium hydroxide | 0.1 |
| Sodium hexametha phosphate | 0.05 |
| Tocopherol acetate | 0.05 |
| p-hydroxybenzoate ester | proper quantity |
| Hydroxypropylmethyl cellulose | 0.3 |
| Polyvinyl alcohol | 0.1 |
| Carboxyvinylpolymer | 0.2 |
| Purified water | balance |

Example 6: Cleansing Cream

| | |
|---|---|
| Microgel dispersion liquid of production example 23 (Microgel in the dispersion liquid: 1.5%, water: 4.05%, dipropylene glycol: 9.45%) | 15 |
| α-olefin oligomer | 20 |
| Vaseline | 5 |
| Glyceryl tri-2-ethylhexanoate | 20 |
| Dimethylpolysiloxane 6cs | 2 |
| Methylphenyl polysiloxane | 15 |
| Batyl alcohol | 0.5 |
| Polyoxyethylene/methylpolysiloxane copolymer | 1 |
| Glycerin | 7 |
| Sorbitol solution (70%) | 18 |
| Polyoxyethylene (60) hydrogenated castor oil | 1 |
| Polyoxyethylene (25) polyoxypropylene glycol (30) | 2 |
| Sodium coconut oil fatty acid methyl taurine | 1 |
| L-serine | 0.1 |
| *Phellodendron amurense* bark extract | 0.1 |
| Sodium alginate | 0.1 |
| Purified water | balance |
| Perfume | proper quantity |

Example 7: Sunscreen Milky Lotion

| | |
|---|---|
| Microgel dispersion liquid of production example 24 (Microgel in the dispersion liquid: 1%, water: 2.7%, dipropylene glycol: 6.3%) | 10 |
| Isododecane | 8 |
| Octyl octanoate | 5 |
| Ethylhexyl methoxycinnamate | 5 |
| Octocrylene | 2 |
| Bis-ethylhexyloxyphenol methoxyphenyl triazine | 3 |
| Oxybenzone | 1 |
| Ethanol | 5 |
| 1,3-buthylene glycol | 5 |
| Triethanol amine | 0.1 |
| Xanthane gum | 0.1 |
| (Acrylate/alkyl acrylate(C10-30)) copolymer | 0.1 |
| Carbomer | 0.1 |
| Tranexamic acid | 2 |
| Talc | 3 |
| Phenoxy ethanol | proper quantity |
| Disodium edetate | proper quantity |
| Purified water | balance |
| Perfume | proper quantity |

Example 8: Cleansing Lotion

| | |
|---|---|
| Microgel dispersion liquid of production example 25 | 10 |
| (Microgel in the dispersion liquid: 1%, water: 2.7%, dipropylene glycol: 6.3%) | |
| Liquid paraffin | 10 |
| Vaseline | 5 |
| Cetanol | 1 |
| Diglycerin | 0.5 |
| 1,3-buthylene glycol | 5 |
| Polyethylene glycol 1500 | 3 |
| Stearic acid | 2 |
| Polyoxyethylene sorbitan (20 E.O.) monolaurate | 0.2 |
| Triethanol amine | 1 |
| Tocopherol acetate | 0.1 |
| Carboxyvinylpolymer | 0.03 |
| Paraben | proper quantity |
| Purified water | balance |

Example 9: Hair Cream

| | |
|---|---|
| Microgel dispersion liquid of production example 2 | 10 |
| (Microgel in the dispersion liquid: 1%, water: 5.4%, dipropylene glycol: 3.6%) | |
| Liquid paraffin | 5 |
| Vaseline | 2 |
| Dimethylpolysiloxane 6cs | 5 |
| Cetanol | 4 |
| Stearyl alcohol | 1 |
| 1,3-buthylene glycol | 10 |
| Polyoxypropylene glyceryl ether | 2 |
| Lipophilic glyceryl monostearate | 2 |
| Polymer JR-400 | 0.5 |
| p-hydroxybenzoate ester | proper quantity |
| Purified water | balance |
| Perfume | proper quantity |

Example 10: Hair Styling Cream

| | |
|---|---|
| Microgel dispersion liquid of production example 3 | 10 |
| (Microgel in the dispersion liquid: 1% water: 5.4%, 1,3-butylene glycol: 3.6%) | |
| Volatile isoparaffin | 5 |
| Dimethylpolysiloxane 6cs | 2 |
| High polymerization methyl polysiloxane | 2 |
| Glycerin | 5 |
| Polyoxyethylene decaglyceryl ether | 5 |
| Isostearic acid | 1 |
| Sodium hydroxide | 0.15 |
| p-hydroxybenzoate ester | proper quantity |
| Phenoxy ethanol | proper quantity |
| Trisodium edetate | proper quantity |
| Xanthane gum | 0.5 |
| Carrageenan | 0.3 |
| Vinyl acetate/vinyl pyrrolidone copolymer | 2 |
| Carboxyvinylpolymer | 0.5 |
| Purified water | balance |

Example 11: Hair Oil Cream

| | |
|---|---|
| Microgel dispersion liquid of production example 4 | 10 |
| (Microgel in the dispersion liquid: 1%, water: 5.4%, isoprene glycol: 3.6%) | |
| Hydrogenated polyisobutene | balance |
| Oxybenzone | proper quantity |
| High polymerization methyl polysiloxane | 10 |

Example 12: Hair Treatment

| | |
|---|---|
| Microgel dispersion of production example 6 | 10 |
| (Microgel in the dispersion liquid: 1%, water: 1.8%, dipropylene glycol: 7.2%) | |
| Dimethylpolysiloxane 6cs | 2 |
| Cetanol | 0.5 |
| Behenyl alcohol | 3 |
| Glycerin | 3 |
| Cetyl 2-ethylhexanoate | 1 |
| Stearyltrimethylammonium chloride | 0.7 |
| Citric acid | 0.05 |
| Sodium lactate solution | 0.01 |
| Dipotassium glycyrrhizinate | 0.1 |
| Lilium candidum bulb extract | 0.1 |
| Hydroxyethyl cellulose | 0.1 |
| p-hydroxybenzoate ester | proper quantity |
| Purified water | balance |
| Perfume | proper quantity |

Example 13: Emulsion Foundation

| | |
|---|---|
| Microgel dispersion liquid of production example 7 | 10 |
| (Microgel in the dispersion liquid: 1%, water: 1.8%, dipropylene glycol: 7.2%) | |
| Alkyl-modified silicone resin-covered titanium oxide | 9.0 |
| Alkyl-modified silicone resin-covered ultrafine particle titanium oxide (40 nm) | 5.0 |
| Alkyl-modified silicone resin-covered iron oxide (red) | 0.5 |
| Alkyl-modified silicone resin-covered iron oxide (yellow) | 1.5 |
| Alkyl-modified silicone resin-covered iron oxide (black) | 0.2 |
| Polyoxyalkylene-modified organopolysiloxane | 0.5 |
| Decamethylpentacyclosiloxane | 5.0 |
| Octyl p-methoxycinnamate | 5.0 |
| Acryl silicone | 4.0 |
| Dynamite glycerin | 6.0 |
| Xanthane gum | 0.1 |
| Carboxymethyl cellulose | 0.3 |
| Sodium acryloyldimethyl taurine/hydroxyethyl acrylate copolymer (content: 35 to 40% by mass) | 1.5 |
| Ion-exchanged water | balance |

What is claimed is:

1. A production method of raw material for cosmetics consisting of a core-corona microgel dispersion comprising:

the step of a radical polymerization of:

(A) a polyethylene oxide macromonomer having chemical formula (1),

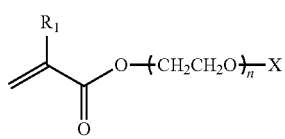

(1)

wherein $R_1$ is an alkyl group having 1 to 3 carbon atoms, n is a number of 8 to 200 and X is H or $CH_3$;

(B) a hydrophobic monomer having chemical formula (2),

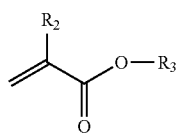
(2)

wherein $R_2$ is an alkyl group having 1 to 3 carbon atoms, and $R_3$ is an alkyl group having 1 to 12 carbon atoms; and (C) a cross-linking monomer having chemical formula (3),

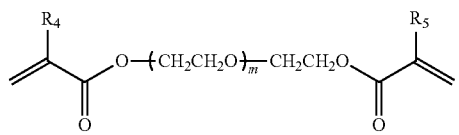
(3)

wherein R4 and R5 are independent alkyl group having 1 to 3 carbon atoms, and m is a number of 0 to 2; and (i) a mole ratio of said polyethylene oxide macromonomer versus said hydrophobic monomer is in the range of 1/10 to 1/250 (mole/mole);

(ii) said cross-linking monomer is in the range of 0.1 to 1.5% by weight relative to said hydrophobic monomer;

(iii) said hydrophobic monomer is a monomer composition comprising at least one $C_1$ to $C_8$ methacrylic acid ester;

(iv) a solvent used for said radical polymerization is a mixed solvent of water and at least one polyol selected from the group consisting of dipropylene glycol, 1,3-butylene glycol, and isoprene glycol, and (v) said mixed solvent of water and polyol has a water versus said polyol ratio that is in the range of 90/10 to 10/90% by mass at 20° C.

2. The production method of raw material for cosmetics, according to claim 1, wherein:
said solvent used for radical polymerization does not contain ethanol.

3. A production method of emulsifier comprising:
said production method of raw material for cosmetics according to claim 1.

4. A production method of white cloudy agent comprising:
said production method of raw material for cosmetics according to claim 1,
wherein said white cloudy agent does not contain ethanol.

5. A production method of emulsifier comprising:
said production method of raw material for cosmetics according to claim 2.

6. A production method of white cloudy agent comprising:
said production method of raw material for cosmetics according to claim 2,
wherein said white cloudy agent does not contain ethanol.

* * * * *